(12) United States Patent
Kahook et al.

(10) Patent No.: US 11,759,356 B2
(45) Date of Patent: Sep. 19, 2023

(54) OPHTHALMIC DEVICE

(71) Applicant: New World Medical, Inc., Rancho Cucamonga, CA (US)

(72) Inventors: Malik Y. Kahook, Denver, CO (US); Eric Porteous, Corona, CA (US); Carlos A. Mendoza, Irvine, CA (US)

(73) Assignee: New World Medical, Inc., Rancho Cucamonga, CA (US)

( * ) Notice: Subject to any disclaimer, the term of this patent is extended or adjusted under 35 U.S.C. 154(b) by 487 days.

(21) Appl. No.: 16/940,147

(22) Filed: Jul. 27, 2020

(65) Prior Publication Data

US 2020/0352784 A1 Nov. 12, 2020

Related U.S. Application Data

(63) Continuation of application No. 16/707,483, filed on Dec. 9, 2019, now Pat. No. 10,722,397, which is a
(Continued)

(51) Int. Cl.
*A61F 9/007* (2006.01)
*A61M 5/315* (2006.01)
(Continued)

(52) U.S. Cl.
CPC ....... *A61F 9/00781* (2013.01); *A61M 5/3134* (2013.01); *A61M 5/31585* (2013.01); *A61M 2005/14533* (2013.01)

(58) Field of Classification Search
CPC ...... A61F 9/00781; A61F 9/00; A61F 9/0008; A61F 9/0017; A61F 9/0026;
(Continued)

(56) References Cited

U.S. PATENT DOCUMENTS 2,156,023 A 4/1939 McKay
2,725,877 A 12/1955 David et al.
(Continued)

FOREIGN PATENT DOCUMENTS

CA 2101837 A1 2/1995
CN 101641125 A 2/2010
(Continued)

OTHER PUBLICATIONS

International Search Report and Written Opinion for Application No. PCT/US2019/56480, dated Mar. 4, 2020, 23 pages.
(Continued)

*Primary Examiner* — Dung T Ulsh
(74) *Attorney, Agent, or Firm* — Morgan, Lewis & Bockius LLP

(57) ABSTRACT

An ophthalmic device including a cannula having a cannula distal end, a lumen, and one or more orifices coupled to the lumen is provided. The cannula is configured to deliver a fluid. A sleeve is disposed around the cannula and has a sleeve distal end. A handle is coupled to the sleeve and the cannula, the handle having an actuator. An internal mechanism is coupled to the actuator and configured to retract the sleeve relative to the cannula. The internal mechanism includes a follower fixedly coupled to the sleeve and moveable between distal and proximal positions, and a release member movable between an activated position and a release position. The release member is coupled to the actuator and configured to release a force that urges the follower from the distal position to the proximal position when the release member moves from the activated position to the release position.

20 Claims, 27 Drawing Sheets

Related U.S. Application Data continuation of application No. PCT/US2019/056480, filed on Oct. 16, 2019.

(60) Provisional application No. 62/750,151, filed on Oct. 24, 2018.

(51) Int. Cl.
*A61M 5/31* (2006.01)
*A61M 5/145* (2006.01)

(58) Field of Classification Search
CPC ............ A61M 5/3134; A61M 5/31585; A61M 2005/14533; A61M 25/0136; A61M 2025/0687
See application file for complete search history.

(56) References Cited

U.S. PATENT DOCUMENTS

| | | | |
|---|---|---|---|
| 4,685,910 A | 8/1987 | Schweizer | |
| 5,163,915 A | 11/1992 | Holleron | |
| 6,010,485 A | 1/2000 | Buch-Rasmussen et al. | |
| 10,213,555 B1 | 2/2019 | Carranza et al. | |
| 10,729,584 B2 | 8/2020 | Kahook et al. | |
| 11,147,709 B2 | 10/2021 | Kahook et al. | |
| 2001/0008961 A1 | 7/2001 | Hecker et al. | |
| 2001/0037087 A1 | 11/2001 | Knauer | |
| 2006/0276753 A1 | 12/2006 | Kronestedt et al. | |
| 2007/0073275 A1 | 3/2007 | Conston et al. | |
| 2007/0191925 A1* | 8/2007 | Dorn ................. A61F 2/95 623/1.12 | |
| 2008/0221530 A1 | 9/2008 | Glejbol et al. | |
| 2010/0211079 A1* | 8/2010 | Aramant ............... A61F 9/0017 604/521 | |
| 2012/0123434 A1 | 5/2012 | Grabner et al. | |
| 2012/0165734 A1 | 6/2012 | Auld et al. | |
| 2012/0310111 A1 | 12/2012 | Schacar et al. | |
| 2013/0197592 A1* | 8/2013 | Mafi ................. A61B 17/3421 606/323 | |
| 2013/0253402 A1 | 9/2013 | Badawi et al. | |
| 2013/0253528 A1 | 9/2013 | Haffner et al. | |
| 2013/0267931 A1 | 10/2013 | Nazzaro et al. | |
| 2013/0281908 A1 | 10/2013 | Schaller et al. | |
| 2013/0297011 A1 | 11/2013 | Morris et al. | |
| 2014/0039456 A1 | 2/2014 | Lerner | |
| 2014/0236098 A1 | 8/2014 | Mica et al. | |
| 2014/0257241 A1 | 9/2014 | Sutkin et al. | |
| 2015/0065940 A1* | 3/2015 | Rangel-Friedman ..................... A61F 9/00781 604/8 |
| 2015/0133946 A1 | 5/2015 | Horvath et al. | |
| 2016/0074211 A1 | 3/2016 | Ko et al. | |
| 2016/0151204 A1 | 6/2016 | Haffner et al. | |
| 2016/0153213 A1 | 6/2016 | Huang | |
| 2016/0169490 A1 | 6/2016 | Kijima et al. | |
| 2016/0287438 A1 | 10/2016 | Badawi et al. | |
| 2016/0325050 A1 | 11/2016 | Gonçalves | |
| 2017/0181892 A1 | 6/2017 | Kahook et al. | |
| 2017/0216092 A1* | 8/2017 | Singh ................. A61M 25/01 | |
| 2017/0296753 A1 | 10/2017 | Rowe et al. | |
| 2018/0028358 A1 | 2/2018 | Andino et al. | |
| 2018/0168863 A1* | 6/2018 | Kahook ............... A61F 9/00781 | |
| 2018/0235660 A1 | 8/2018 | Bacich | |
| 2018/0339110 A1 | 11/2018 | Stiffler | |
| 2019/0105077 A1* | 4/2019 | Kalina, Jr. ............. A61F 9/007 | |
| 2019/0274825 A1* | 9/2019 | Kanner ................. A61F 2/167 | |

FOREIGN PATENT DOCUMENTS

| | | |
|---|---|---|
| CN | 103598767 A | 2/2014 |
| CN | 104105513 A | 10/2014 |
| CN | 104508787 A | 4/2015 |
| CN | 104540472 A | 4/2015 |
| CN | 106029019 A | 10/2016 |
| EP | 3064241 A1 | 9/2016 |
| GB | 527971 A | 10/1940 |
| JP | 2010189781 A | 9/2010 |
| WO | WO-0051668 A1 | 9/2000 |
| WO | WO-2015005313 A1 | 1/2015 |
| WO | WO-2016010810 A2 | 1/2016 |
| WO | WO-2016159999 A1 | 10/2016 |
| WO | WO-2016186965 A2 | 11/2016 |
| WO | WO-2017180480 A1 | 10/2017 |

OTHER PUBLICATIONS

International Search Report and Written Opinion for Application No. PCT/US2019/56482, dated Feb. 7, 2020, 12 pages.
Invitation to Pay Additional Fees for Application No. PCT/US2019/56480, dated Dec. 13, 2019, 2 pages.
Invitation to Pay Additional Fees for Application No. PCT/US2019/56482, dated Dec. 13, 2019, 2 pages.
Extended European Search Report for Application No. 19875683.5, dated Jul. 22, 2022, 9 pages.
Extended European Search Report for Application No. 19876723.8, dated Jun. 14, 2022, 9 pages.
Chinese Office Action for Application No. 201980085570.6, dated Feb. 11, 2023, 18 pages including translation.
Chinese Office Action for Application No. 201980085388.0, dated May 19, 2023, 28 pages including translation.

* cited by examiner

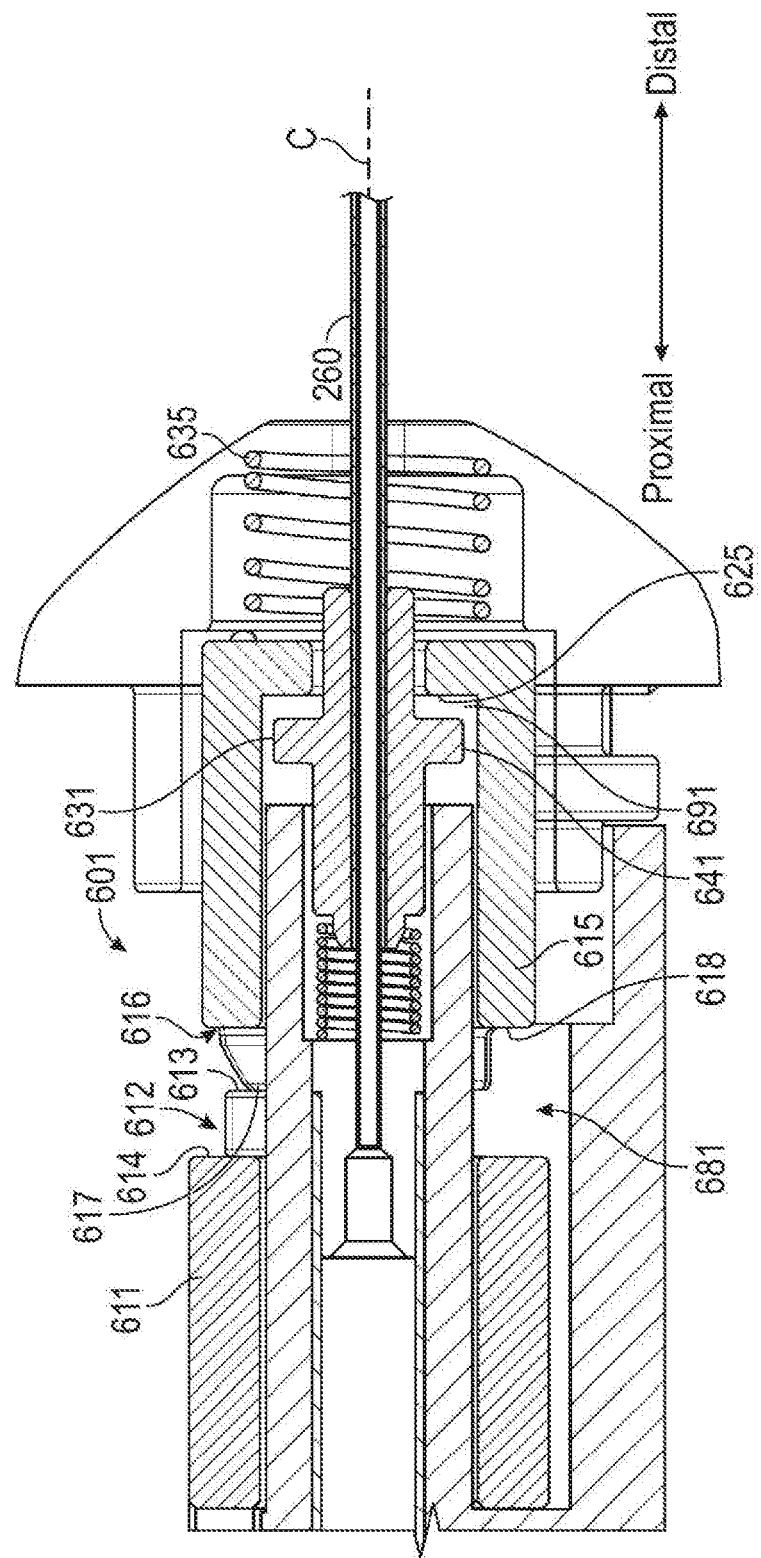

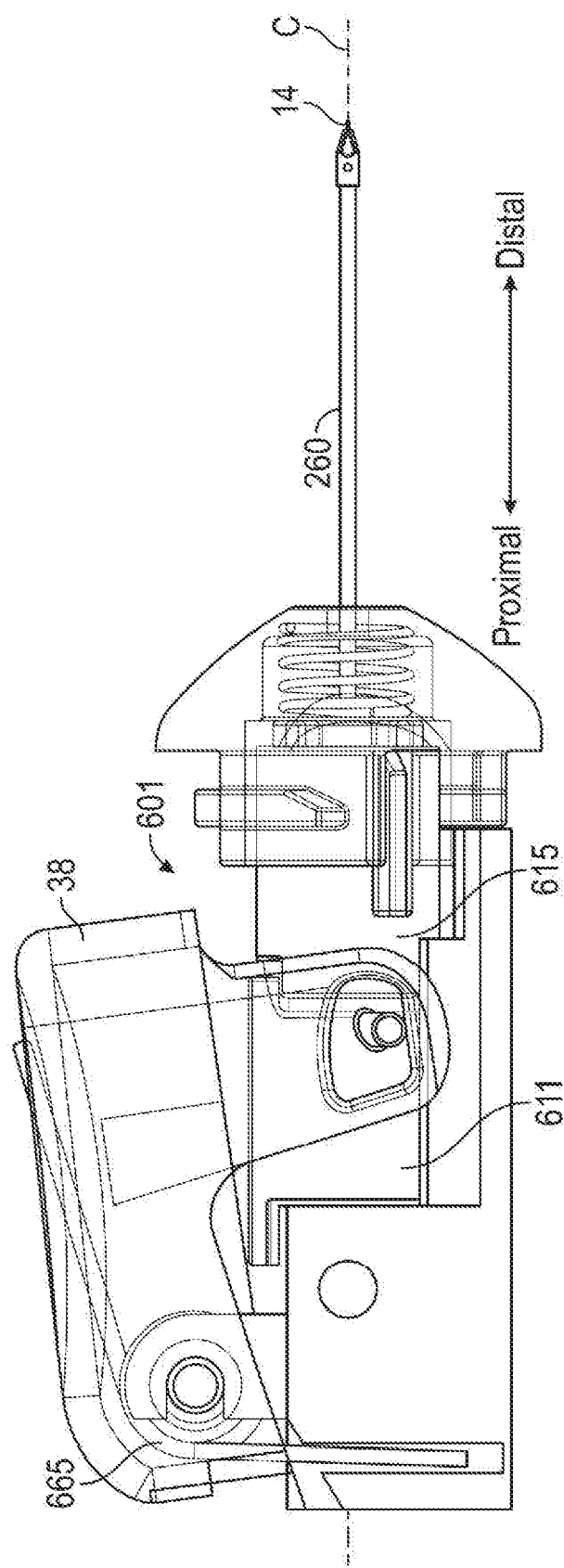

OPHTHALMIC DEVICE

CROSS-REFERENCE TO RELATED APPLICATIONS

This application is a continuation of U.S. patent application Ser. No. 16/707,483, entitled "OPHTHALMIC DEVICE," filed Dec. 9, 2019, which issued as U.S. Pat. No. 10,722,397 on Jul. 28, 2020, which is a continuation of and claims priority to International Patent Application No. PCT/US2019/056480, entitled "OPHTHALMIC DEVICE," filed Oct. 16, 2019, which claims the benefit of priority under 35 U.S.C. § 119 from U.S. Provisional Application No. 62/750,151, entitled "OPHTHALMIC DEVICE," filed Oct. 24, 2018, the entirety of which are incorporated herein by reference.

TECHNICAL FIELD

The present disclosure generally relates to medical devices and procedures, and more particularly, to an ophthalmic device.

BACKGROUND

Glaucoma is a disease resulting from an increase in intraocular eye pressure (IOP). IOP may increase when natural drainage of the eye (e.g., drainage of the humus of the eye) is prevented, reduced, or otherwise blocked. Cavities in front of (e.g., on top of) the lens of the eye are filled with a viscous fluid called aqueous humor. A continuous flow of aqueous humor through the eye provides nutrition to portions of the eye (e.g., the cornea and the lens) that have no blood vessels. This flow of aqueous humor also removes waste (e.g., foreign object debris) from these tissues. In a healthy eye, a stream of aqueous humor drains out of the anterior chamber of the eye through the trabecular meshwork and into Schlemm's canal as new aqueous humor is secreted by the epithelial cells of the ciliary body. The drained aqueous humor enters the venous blood stream from Schlemm's canal and is carried along with the venous blood leaving the eye. When the natural drainage mechanisms of the eye (e.g., Schlemm's canal and/or the trabecular meshwork) stop functioning properly, the IOP begins to increase.

SUMMARY

One or more embodiments the present disclosure provides an ophthalmic device including a cannula having a cannula distal end, a lumen, and one or more orifices coupled to the lumen, the cannula configured to deliver a fluid; a sleeve disposed around the cannula and having a sleeve distal end; a handle coupled to the sleeve and the cannula, the handle having an actuator; and an internal mechanism coupled to the actuator and configured to retract the sleeve relative to the cannula. The internal mechanism includes a follower fixedly coupled to the sleeve and moveable between distal and proximal positions and a release member movable between an activated position and a release position, the release member coupled to the actuator and configured to release a force that urges the follower from the distal position to the proximal position when the release member moves from the activated position to the release position.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

FIG. 2A shows the inner cannula covered by the sleeve and FIG. 2B shows inner cannula protruding from the sleeve.

FIG. 3A shows the sleeve in a distal position and FIG. 3B shows the sleeve in a retracted proximal position.

FIG. 4A shows an example of a sleeve sized to abut against a trabecular meshwork over a Schlemm's canal and a more rigid anatomy neighboring the Schlemm's canal. FIG. 4B shows an example of a sleeve sized to collapse the trabecular meshwork into the Schlemm's canal.

FIG. 5A is a perspective view of the sleeve, FIG. 5B is a top view of the sleeve, and FIG. 5C is a side view of the sleeve.

FIG. 6A is a perspective view of the sleeve, FIG. 6B is a top view of the sleeve, and FIG. 6C is a side view of the sleeve.

FIG. 7A is a perspective view of cannula, FIG. 7B is a top view of the cannula as implemented in FIG. 7A, and FIG. 7C is a side view of cannula as implemented in FIG. 7A.

FIG. 9A shows the mechanism in a starting position, FIG. 9B shows the mechanism in an intermediate position, and FIG. 9C shows the mechanism in a released position.

FIG. 10A shows the mechanism in a starting position, FIG. 10B shows the mechanism in an intermediate position, and FIG. 10C shows the mechanism in a released position.

FIGS. 11A and 11B show the mechanism in a starting position, FIG. 11C shows the mechanism in a released position, and FIG. 11D shows the mechanism in a reset position.

FIGS. 12A-12E are perspective, side and cross-sectional side views showing an example of a mechanism that can be configured to retract a sleeve in an ophthalmic device. FIGS. 12A-12C show the mechanism in a starting position, and FIGS. 12D-12E show the mechanism in a released position.

FIG. 14A shows a nut and a pump of the mechanism with a linkage removed, FIG. 14B shows a linkage in an initial position, and FIG. 14C shows the linkage in an actuated position.

FIG. 15A shows the ophthalmic device entering an anterior chamber and FIG. 15B shows the ophthalmic device injecting a fluid into a Schlemm's canal.

DETAILED DESCRIPTION

Figure 1:
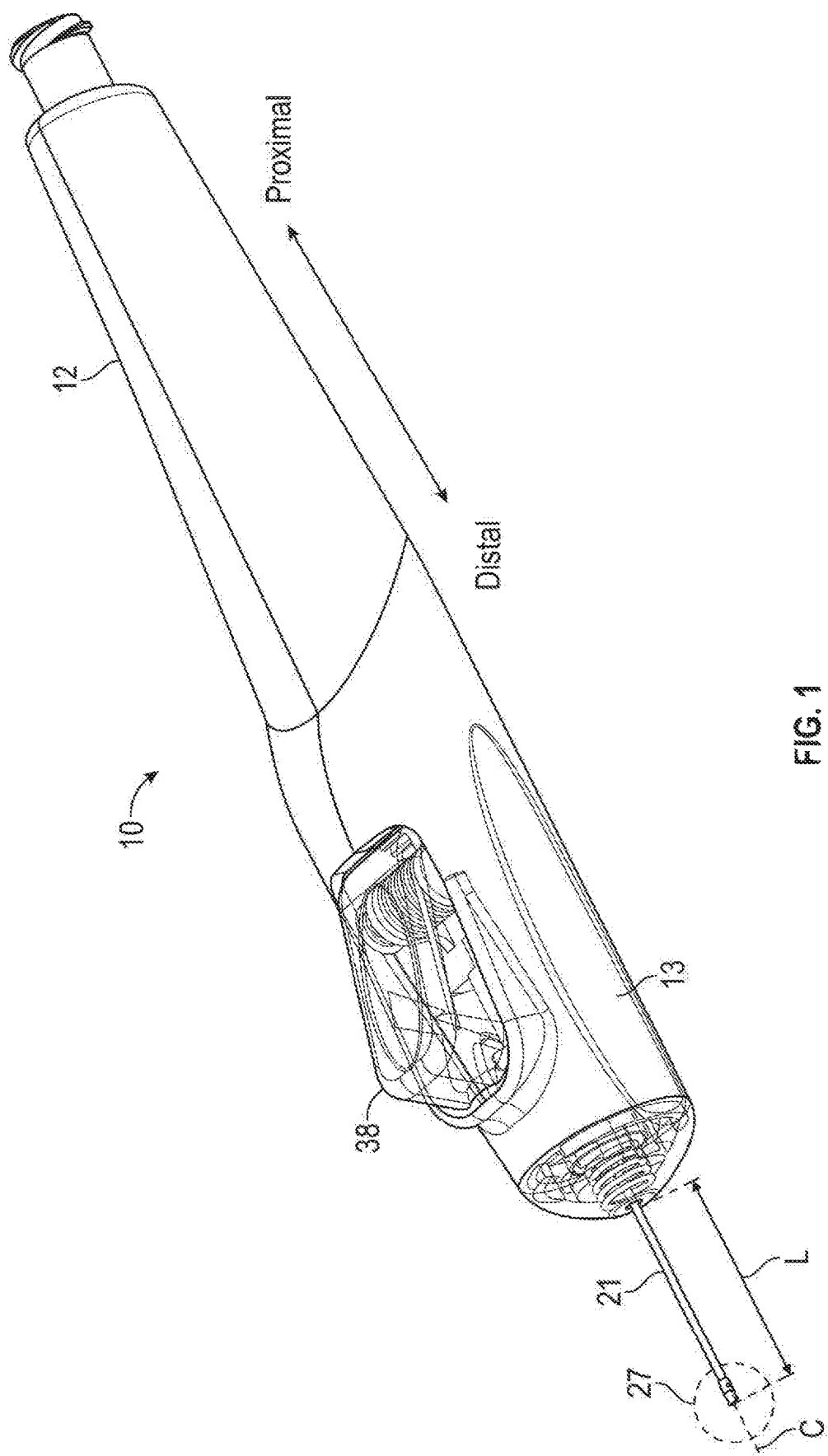
FIG. 1 is a perspective view showing an example of an ophthalmic device.

The following detailed description is exemplary and explanatory only and is not restrictive of the features, as claimed. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +1-5% of a stated value. The term "distal" refers to a portion farthest away from a user when introducing a device into a subject. By contrast, the term "proximal" refers to a portion closest to the user when placing the device into the subject.

Embodiments discussed below relate to a medical device, such as an ophthalmic device configured for use in the treatment of glaucoma or other eye conditions, and related methods of use. According to some embodiments, the ophthalmic device can have a distal end including a cannula. The cannula can include an inner lumen and one or more outflow orifices configured for delivery of viscoelastic fluid or other substance into a target site of a patient, such as a Schlemm's canal.

According to some embodiments, a tip of the cannula can include a collar disposed around an outer surface of the cannula. The collar can be configured to interact with intraocular tissue in an aqueous outflow pathway of a patient's eye to facilitate positioning of the cannula or facilitate fluid transfer with respect to the eye. For example, the collar can include a radially protruding lip that is fixed or movable to a position proximal to the orifices to provide a structure that facilitates positioning of the orifices of the cannula within or near Schlemm's canal.

According to some embodiments, the collar can be implemented as part of a retractable sleeve. The sleeve can be disposed around the cannula and configured to retract relative to the cannula to pull patient tissue via a suction effect. For example, manipulation of a button or other actuator component disposed on a handle of the device can be configured to retract the sleeve to pull a trabecular meshwork over and around the cannula to penetrate the meshwork with the cannula and open up the canal to facilitate fluid delivery therein.

According to some embodiments, a mechanism can be configured to retract the sleeve or otherwise move a component of the ophthalmic device with a relatively quick and sharp snapping motion. Such a motion can, for example, facilitate suction of the patient's tissue and penetration thereof by the cannula. Additionally or alternatively, the mechanism can operate a pump to inject the fluid or substance through the cannula in concert with the retraction of the sleeve.

These and other embodiments are discussed below in relation to particular examples illustrated in FIGS. 1-9B. However, various modifications and alternative applications will be appreciated by those skilled in the art. Thus, the detailed description provided with respect to these figures as well as the description provided above should not be construed as limiting but rather serves to explain various concepts associated with this disclosure.

FIG. 1 shows an example of a medical device, and more particularly, shows an example of an ophthalmic device 10. In the example shown, the ophthalmic device 10 is configured as a medical instrument or minimally invasive surgical instrument configured to interact with ocular tissue to facilitate injection of a substance into a Schlemm's canal or other intraocular site of an eye of a patient. However, while examples herein are described with reference to ophthalmic instruments and procedures, it will be appreciated that teachings of the ophthalmic device 10 can be readily applied to or adapted for any of a variety of other medical and non-medical applications. These can include, for example, other medical procedures involving interactions with patient tissue other than in the patient's eye, and other non-medical applications involving fluid injection or transfer.

Referring to FIG. 1, the ophthalmic device 10 can include a handle 12 coupled to an ocular component 21. The ocular component 21 is generally configured for interacting with ocular tissue and/or insertion into an intraocular cavity, such as the anterior chamber of an eye of a patient. The ocular component 21 can be configured to facilitate fluid delivery, tissue manipulation, and/or other interactions with the eye of the patient.

As shown in the example of FIG. 1, the ocular component 21 can include an elongated tubular member protruding from a distal end of the handle 12 and defining a central longitudinal axis C. The ocular component 21 can have a working length L and a diameter that permits insertion into the anterior chamber through a corneal incision or other incision on an eye of a patient. The working length L described herein can be defined as the exposed length or distance of the ocular component 21 protruding from the handle 12, extending from the distal end of the handle 12 to the distal end of the ocular component 21. The working length L can be, for example, in the range of between about 16 millimeters (mm) and 40 mm, or more particularly about 18 mm, although it contemplated that other dimensions outside of these examples may be suitable in various implementations. The diameter may vary across the working length L or be constant throughout the working length L and can be, for example, in the range of about 100 micrometers (μm) to 1000 μm, or more particularly about 700 μm, although it is contemplated that other dimensions outside of these example may be suitable in various implementations. As shown in the example of FIG. 1, the ocular component 21 can be implemented with a straight geometry (defining a straight central axis C), or the ocular component 21 can be implemented with a curved and/or bent geometry.

With continued reference to FIG. 1, the handle 12 can be implemented as a main body of the ophthalmic device 10 and can be configured to be manipulated by the hand of a user or other operator. For example as shown in FIG. 1, the handle 12 can be implemented as an elongated tubular member having a distal end and a proximal end opposite to the distal end. This can, for example, facilitate gripping or manipulation of the handle 12 using a pencil-grip by a surgeon, although it is contemplated that handle 12 can be implemented with other shapes and configurations, such as pistol-shaped arrangements and/or finger loops. An outer surface of the handle 12 can include finger grips 13 having a contoured shape and/or textured surface (e.g., knurled, ribbed, or other surface textures) to facilitate grasping of the handle 12 by the user. Implementations are also contemplated in which the outer surface of the handle 12 has a straight non-contoured shape and/or a smooth outer surface.

The handle 12 can include or be coupled to an actuator 38. The actuator 38 can be coupled to one or more moving parts of the ophthalmic device 10 to provide one or more operative functions that facilitate performance of an ophthalmic procedure using the device. For example, the actuator 38 can be configured to move one or more parts of the ocular component 21 independently of the handle 12 and/or move two or more moving parts of the ocular component 21 independently of each other. Additionally or alternatively, the actuator 38 can be configured to actuate a pump, plunger, and/or squeeze mechanism for fluid transfer through the ocular component 21. The actuator 38 can, for example, be configured to move the part(s) directly or via an internal mechanism disposed in the handle 12.

In the example shown in FIG. 1, the actuator 38 is implemented as or otherwise includes a mechanical push button disposed on the handle 12 and movable between an un-pressed and pressed position. The push button is shown disposed on a lateral side of the handle 12 which can, for example, facilitate actuation by a surgeon or other user using their thumb and/or index finger when the handle 12 is grasped in the hand of the user during a procedure. Additionally or alternatively, implementations are contemplated in which the push button is disposed in other locations, such as a proximal end of the handle, for example. Implementations are also contemplated in which, instead of or in addition to the push button, the actuator 38 includes a slider, roller wheel, squeeze bulb, and/or any other suitable mechanism that can be manipulated by a user or other operator to actuate a moving part of the ophthalmic device 10.

Figure 2A:
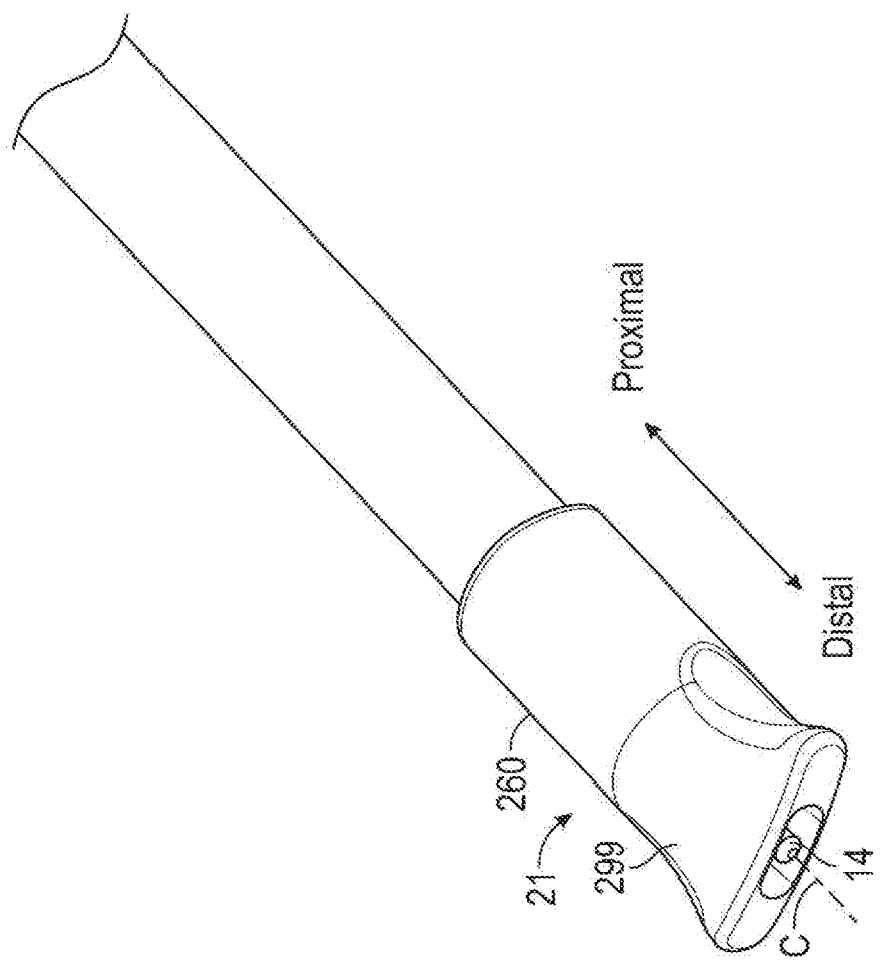
FIGS. 2A-2B are perspective views showing a distal end of an example of an ophthalmic device that has an inner cannula surrounded by a sleeve.
Figure 2B:
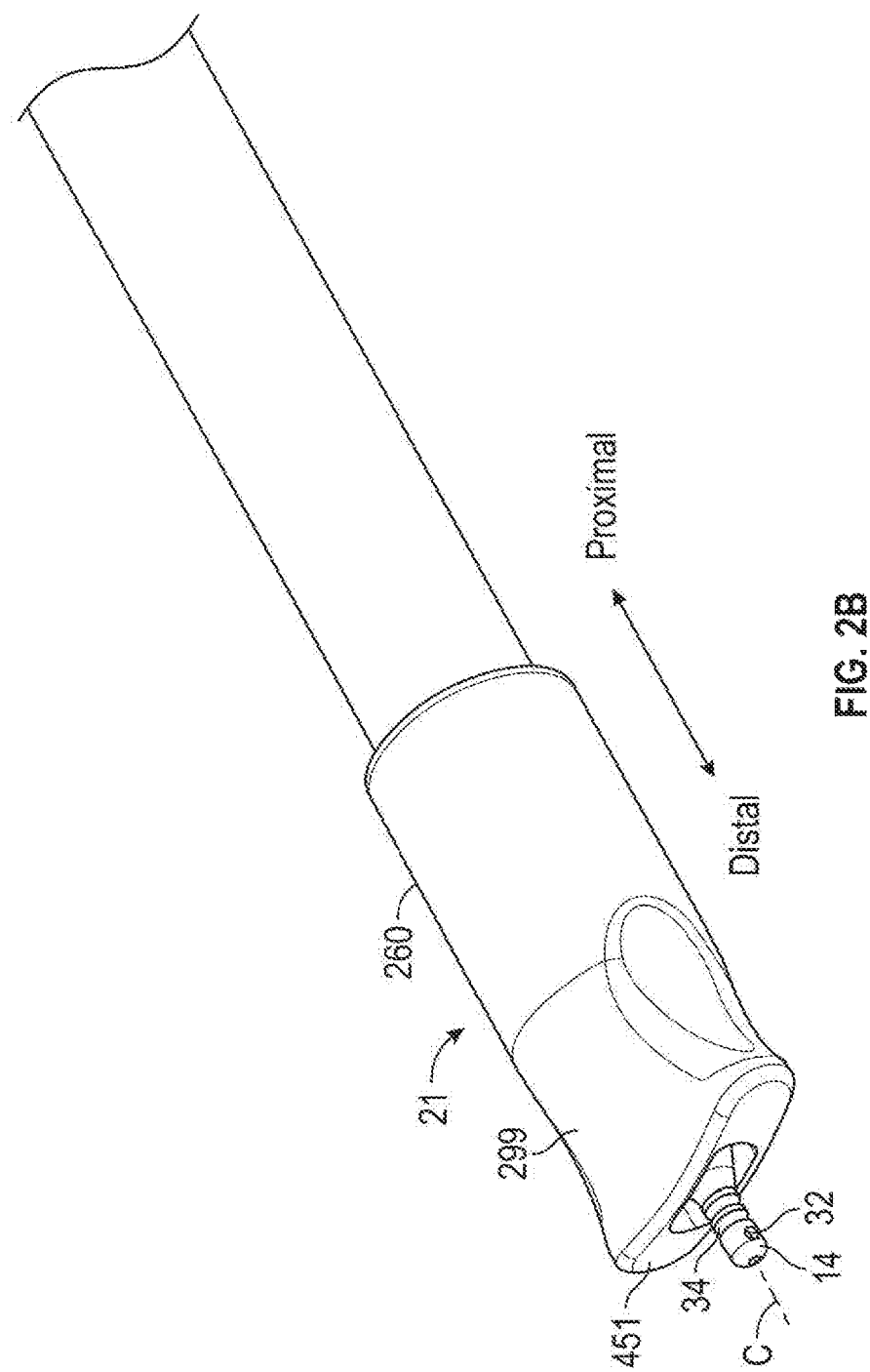

FIGS. 2A and 2B are enlarged views showing an example of an ocular component 21 that can be included in the ophthalmic device 10. FIGS. 2A and 2B show a distal portion 27 of the ocular component 21 as indicated in FIG. 1.

In the example shown in FIGS. 2A and 2B, the ocular component 21 includes a cannula 14 and a sleeve 260 (also sometimes referred to herein as a "sheath"). The sleeve 260 is disposed around the cannula 14 and the cannula 14 is disposed within the sleeve 260. The cannula 14 and the sleeve 260 can, for example, each be implemented as substantially tubular components in which the cannula 14 is disposed coaxially with the sleeve 260 and both the cannula 14 and the sleeve 260 are disposed about the central axis C. The cannula 14 and/or sleeve 260 can, for example, each have a working length equivalent to the working length L of the ocular component 21.

The cannula 14 and the sleeve 260 can be configured for relative movement with respect to each other. For example as shown in FIGS. 2A and 2B, the cannula 14 and the sleeve 260 can be moveable with respect to each other between a first configuration (shown in FIG. 2A) in which the distal end of the cannula 14 is substantially covered or encased by the sleeve 260, and a second configuration (shown in FIG. 2B) in which the distal end of the cannula 14 protrudes distally from the distal end of the sleeve 260. The relative movement can be accomplished by, for example, retraction of the sleeve 260 in a proximal direction independently of the cannula 14 and the handle 12, and/or by deployment of the cannula 14 in a distal direction independently of the sleeve 260 and the handle 12. The actuator 38 can be operatively coupled to the cannula 14 and/or sleeve 260 to move the cannula 14 and/or sleeve 260 with respect to a fixed component of the handle 12.

The cannula 14 can be configured to transfer a fluid or other substance. For example, the cannula 14 can be configured for injection of a viscoelastic fluid, such as sodium hyaluronate or chondroitin sulfate. Viscoelastic fluid is a highly pliable, gel-like material which helps provide enough space for adequate drainage and eye pressure relief by expanding tissue structures away from one another, to re-open or expand a flow path of aqueous humor. Viscoelastic fluid also may clear an obstructed view by expanding bleeding structures away from one another to improve visualization. It is also contemplated that the cannula 14 can be utilized to deliver stem cells, medicaments, gases (e.g., SF6 or C3F8), and/or dyes (e.g., trypan blue dye). Injected stem cells, for example, can initiate growth of healthy tissues within the eye (e.g., to develop healthy trabecular meshwork to enhance drainage of aqueous humor there through). Injected dye, for example, can flow through the trabecular meshwork to enhance visualization of aqueous humor fluid flow to determine which areas, if any, of the trabecular meshwork remain blocked, collapsed, or otherwise impede flow of aqueous humor. Further, while examples are described with respect to the injection of substances, it is contemplated that the cannula 14 can additionally or alternatively be utilized to withdraw substances, such as to withdraw tissue, blood, aqueous humor, or other substances out of a Schlemm's canal or other part of an eye.

As shown in FIG. 2B, the cannula 14 can be implemented as a blunt microcannula having a rounded, unsharpened, or otherwise atraumatic tip at its distal end. While implementations are also contemplated in which the cannula 14 is implemented with a sharp needle or traumatic tip at its distal end, the blunt cannula can facilitate penetration of porous patient tissue, such as a trabecular meshwork, while mitigating risk of undesired trauma to surrounding tissue.

The cannula 14 can include one or more orifices 32 disposed on a distal portion of the cannula 14, e.g., disposed on or near the cannula distal end. The one or more orifices 32 can provide one or more fluid transfer ports configured to transfer a fluid or other substance. For example, the one or more orifices 32 can be configured to provide outflow ports for delivery of a viscoelastic substance to a Schlemm's canal of an eye of a patient. As shown in the example of FIG. 2B, the one or more orifices 32 can be disposed on a lateral side of the cannula 14 which can provide one or more fluidic channels through a sidewall of the cannula 14 in a direction transverse to the central axis C. Alternatively, other implementations are contemplated in which the orifices are disposed along the central axis C and/or in any other one or more suitable positions to transfer fluid to and/or from an intended target site. The orifices can each have a diameter of between 30 μm to 70 μm, or such as about 50 μm or about 60 μm, although it is contemplated that other orifice diameters outside of these ranges may be suitably used in various implementations. The cannula 14 may include one or more grooves 34 disposed on a distal portion of the cannula 14.

As shown for example in FIGS. 2A and 2B, relative movement between the sleeve 260 and the cannula 14 can be configured to selectively cover and uncover one or more of the orifices 32 with the sleeve 260. For example, when in the first configuration shown in FIG. 2A, the distal end of the sleeve 260 can be disposed at a first axial position distal to the orifice(s) 32 so as to cover or surround the orifice(s) 32, and when in the second configuration shown in FIG. 2B, the distal end of the sleeve 260 can be disposed at a second axial position proximal to the orifice(s) 32 so as to expose the orifice(s) 32 outside of the distal end of the sleeve 260.

The ophthalmic device 10 can further include a collar 299 disposed about a circumference of a tip of the cannula 14 at or near the cannula distal end. For example as shown in FIGS. 2A and 2B, the collar 299 can be an integral part of the sleeve 260 or otherwise fixedly coupled to the sleeve 260 at the sleeve distal end, in which case collar 299 can move together with the sleeve 260 so that the collar 299 and the cannula 14 are movable relative to each other. The collar 299 can provide a structure disposed about a circumference of the cannula 14 (e.g., on or around an outer diameter of the cannula 14) that is configured to interact with patient tissue so as to facilitate placement of the cannula 14. For example, a face 451 of the collar 299 at the distal end of the collar can be configured to manipulate a trabecular meshwork and/or provide a guiding constraint that abuts the trabecular meshwork and/or other tissue neighboring Schlemm's canal. This guiding constraint may, for example, facilitate placement of the orifice(s) 32 to a desired penetration depth within the canal.

In the example shown in FIGS. 2A and 2B, the collar 299 is included as part of a distal portion of the sleeve 260. When the sleeve 260 and the cannula 14 are in the second configuration shown in FIG. 2B, the face 451 of the collar 299 provides a lip that protrudes radially outward away from an outer diameter of the cannula 14. The lip can abut a trabecular meshwork or other tissue neighboring Schlemm's canal so that the penetration depth of the cannula 14 is constrained or guided by a predetermined distance between the distal end of the cannula 14 and the lip (or the face 451 or distal end of the collar 299) when the device is in the second configuration.

Figure 3A:
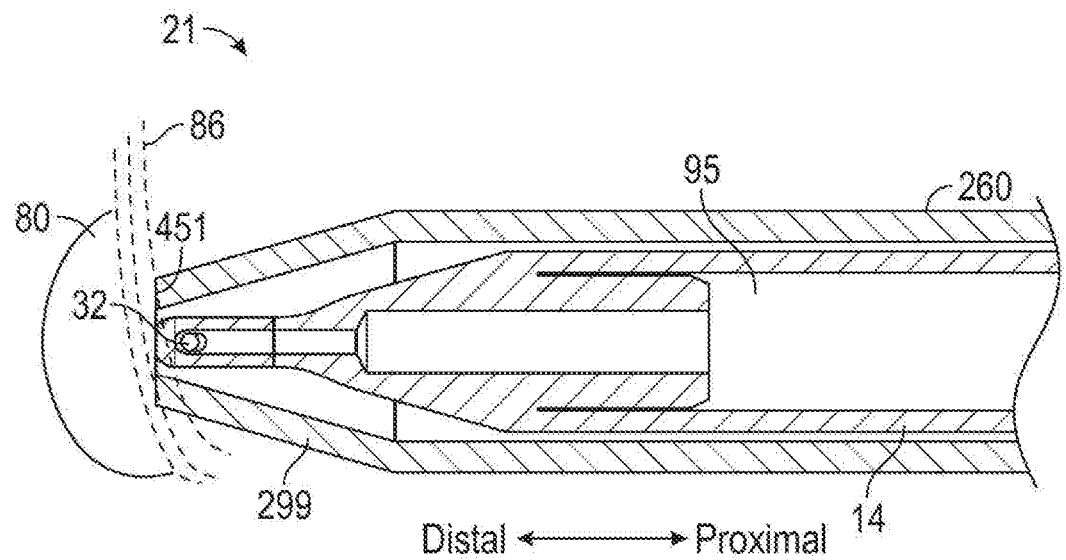
FIGS. 3A-3B are longitudinal section views showing a retractable sleeve interacting with ocular tissue.
Figure 3B:
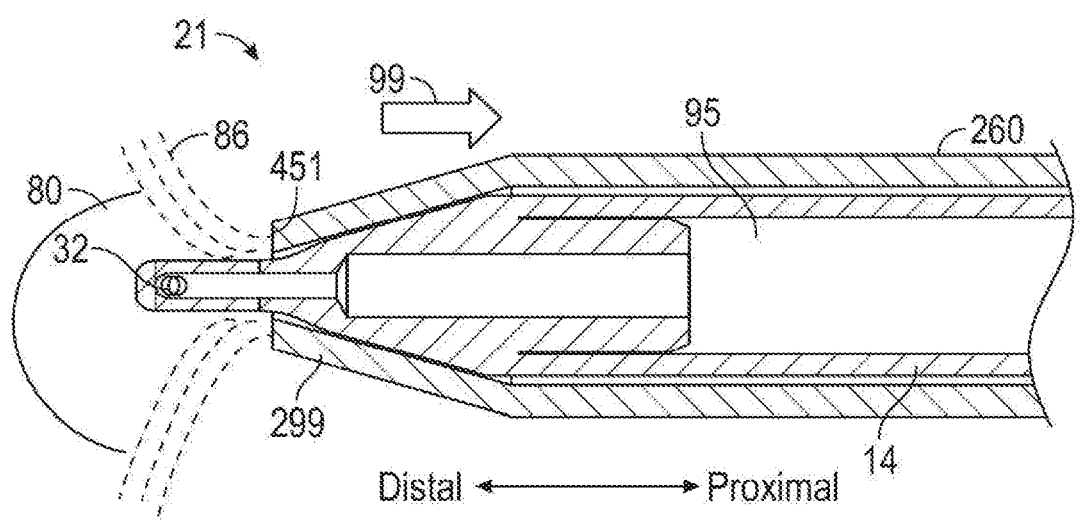

FIGS. 3A and 3B are longitudinal section views showing a distal portion 27 of an example of an ocular component 21 interacting with ocular tissue. FIG. 3A shows the sleeve 260 in a distal position, and FIG. 3B shows the sleeve 260 in a retracted position in which the sleeve 260 is retracted in a proximal direction 99 as shown by the arrow.

As shown in FIGS. 3A and 3B, the collar 299 at the distal end of the sleeve 260 can be configured to contact patient tissue, and the sleeve 260 can be configured to retract proximally so as to pull patient tissue over the cannula 14. For example, the sleeve 260 can be configured to retract in a proximal direction 99 using a snapping motion (i.e., a sharp and quick motion) so as to create a suction microenvironment over a trabecular meshwork 86 of an eye of a patient when the sleeve 260 and/or collar 299 is pressed against the trabecular meshwork 86. The sleeve 260 via its snapping motion can pull and expand the trabecular meshwork 86 proximally, which may also serve to expand a Schlemm's canal 80 as the trabecular meshwork 86 vaults away from the anterior wall of the canal. Concurrently with the pulling of the trabecular meshwork 86, the distal end of the cannula 14 may be left in place so that the trabecular meshwork 86 passes over the cannula 14 and the cannula 14 pierces or penetrates the trabecular meshwork 86, leaving the orifice(s) 32 in place inside of the Schlemm's canal 80. When the trabecular meshwork 86 is pulled and the orifice (s) 32 are positioned in the Schlemm's canal 80, the ophthalmic device 10 may be configured to deliver a substance into the Schlemm's canal 80 via a lumen 95 in the cannula 14 that is fluidly coupled to the orifice(s) 32. The proximal retraction of the sleeve 260 may beneficially serve to expand the Schlemm's canal 80 and/or otherwise facilitate fluid delivery and/or treatment via penetration by the cannula 14. It is also contemplated that the substance may be injected in some implementations by deploying the cannula 14 distally while the sleeve 260 remains in place, by moving the cannula 14 proximally or distally together with the sleeve 260, and/or by other techniques.

Figure 4A:
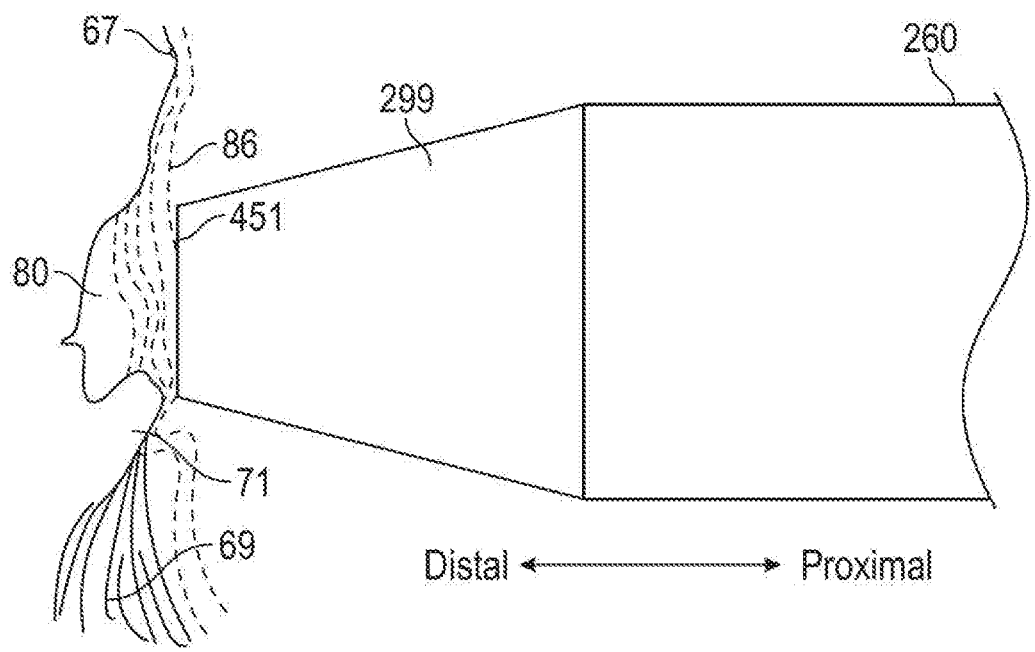
FIGS. 4A-4B are side views showing examples of sleeves interacting with ocular tissue.
Figure 4B:
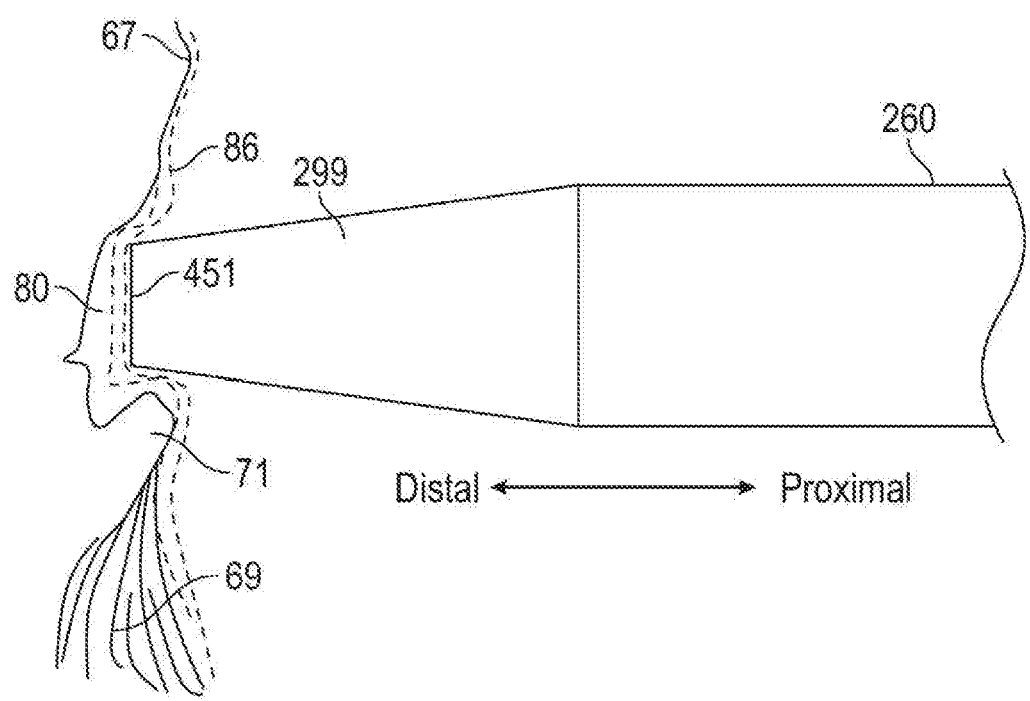

FIGS. 4A and 4B are longitudinal side views showing examples of the sleeve 260 interacting with ocular tissue. FIG. 4A shows a first example of sizing that can be implemented at the distal end of the sleeve 260, and FIG. 4B shows a second example of sizing that can be implemented in the distal end of the sleeve 260. FIGS. 4A and 4B show trabecular meshwork 86 and Schlemm's canal 80 as well as other neighboring eye anatomy, such as a scleral spur 71, ciliary muscle 69, and Schwalbe's line 67.

As shown in both FIGS. 4A and 4B, a size of a distal end of the sleeve 260 (or a size of the face 451 or distal end of the collar 299) can be sufficiently small so as to permit the distal end to be inserted in the iridocorneal angle using an ab interno approach (approach from within the anterior chamber) to abut against and contact the trabecular meshwork 86. In the example shown in FIG. 4A, the size of the distal end of the sleeve 260 is made sufficiently large so that the distal end is configured to abut against both the trabecular meshwork 86 and neighboring anatomy that is more rigid than the trabecular meshwork 86, such as scleral spur 71, so as to substantially prevent collapse of the trabecular meshwork 86 within Schlemm's canal 80 when the distal end is advanced against the trabecular meshwork 86. In the example shown in FIG. 4B, the size of the distal end of the sleeve 260 is made sufficiently small so that the distal end is configured to collapse the trabecular meshwork 86 within Schlemm's canal 80 when the distal end is pressed against the trabecular meshwork 86, e.g., in a region between scleral spur 71 and Schwalbe's line 67. In either example, upon abutting against the trabecular meshwork 86, the distal end may be configured to create a full or partial seal against the trabecular meshwork 86 and/or other ocular tissue together with surrounding fluids such as aqueous humor and/or viscoelastic (e.g., ophthalmic viscoelastic device (OVD)). The ophthalmic device 10 can then be configured to retract the sleeve 260 to pull on the trabecular meshwork 86 as described above with respect to FIGS. 3A and 3B. Further, it is contemplated that the distal end can have an oblong cross sectional shape with a long side sized like that shown in FIG. 4A and a short side sized like that shown in FIG. 4B. The long side can be configured to contact the rigid anatomy upon advancement against the trabecular meshwork 86 when the long side is oriented transverse to the direction in which the trabecular meshwork 86 extends around the lens of the eye, and the short side can be configured to collapse the trabecular meshwork 86 in the Schlemm's canal 80 when the long side is aligned with the direction in which the trabecular meshwork 86 extends.

Figure 5A:
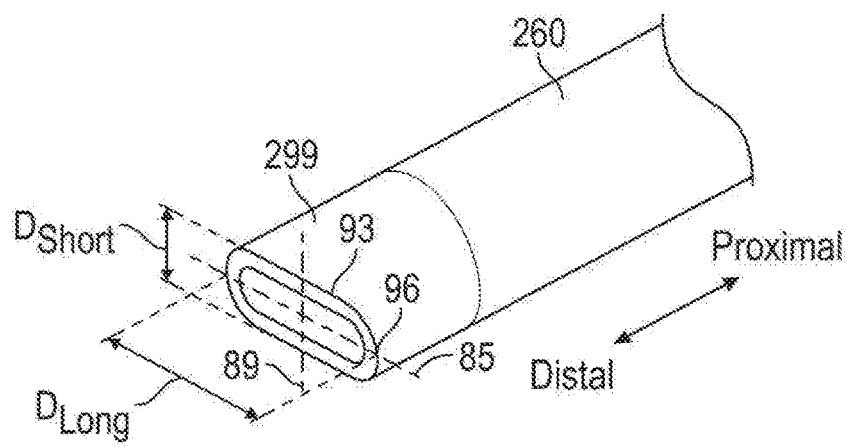
FIGS. 5A-5C are various views showing an example of a sleeve that can be included in an ophthalmic device.
Figure 5B:
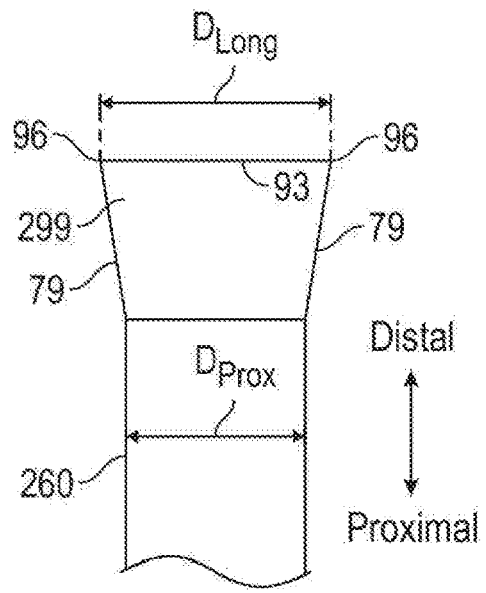
Figure 5C:
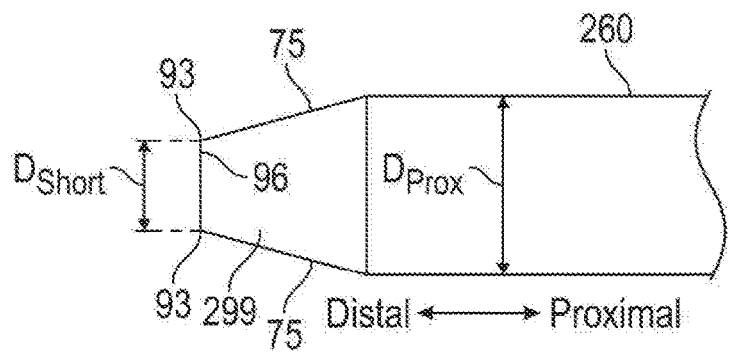

FIGS. 5A-5C are various views of a distal portion of an example of sleeve 260 including collar 299. FIG. 5A is a perspective view of the sleeve 260, FIG. 5B is a top view of the sleeve 260 as implemented in FIG. 5A, and FIG. 5C is a side view of the sleeve 260 as implemented in FIG. 5A.

As shown for example in FIGS. 5A-5C, the collar 299 (e.g., the face 451) and the distal end of the sleeve 260 can have an oblong cross-sectional shape (e.g., an oval, an ellipse, a rounded corner rectangle, or other oblong shape). The oblong shape has a pair of opposing long sides 93 and a pair of opposing short sides 96. The long sides 93 define a long axis 85 of the oblong cross-section and the oblong cross-section has a long outer diameter $D_{LONG}$ along the long axis 85. The short sides 96 define a short axis 89 of the oblong cross-section and the oblong cross-section has a short outer diameter $D_{SHORT}$ along the short axis 89 smaller than the long diameter $D_{LONG}$. As shown for example in FIG. 5B, the collar 299 and the distal end of the sleeve 260 can include a pair of diverging outer surfaces 79 on opposing sides of the sleeve 260 that diverge (or flare radially outward) towards opposing short sides of the distal end of the sleeve 260. As shown for example in FIG. 5C, the collar 299 and the distal end of the sleeve 260 can also include a pair of converging outer surfaces 75 on opposing sides of the sleeve 260 that converge (or taper radially inward) towards opposing long sides of the distal end of the sleeve 260. As a result, the long outer diameter $D_{LONG}$ can be greater than the outer diameter $D_{PROX}$ of a proximal portion of the sleeve 260, while the short outer diameter $D_{SHORT}$ can be smaller than the outer diameter $D_{PROX}$ of a proximal portion. The distal end of the sleeve 260 can be sized to fit within an iridocorneal angle (angle formed between the iris and the cornea) to permit the distal tip to contact or press against the trabecular meshwork and/or scleral spur of an eye, and the above described orientation with flared configuration along the long axis 85 can be useful to, for example, indicate a preferential orientation of the sleeve tip for the surgeon to properly place the tip to avoid over compressing the trabecular meshwork and/or Schlemm's canal.

The collar 299 and/or the sleeve 260 can further be configured as a light guide to enhance visualization when placed in the eye. For example, a light source such as one or more light emitting diode (LEDs) can be disposed in the handle 12 or otherwise positioned on the ophthalmic device 10 proximal to the distal end of the sleeve 260. The light source can be configured to couple visible light into the sidewalls of the sleeve 260 so that the light propagates through the sidewalls of the sleeve 260 via total internal reflection (TIR) and out of the distal end or distal portion of the sleeve 260 (e.g., out the face 451). Additionally or alternatively, the sleeve 260 can be made transparent or include one or more transparent windows to facilitate visualization of the sleeve 260 and/or the cannula 14, although it is contemplated that the sleeve 260 can be made wholly opaque to visible light in other implementations.

Figure 6A:
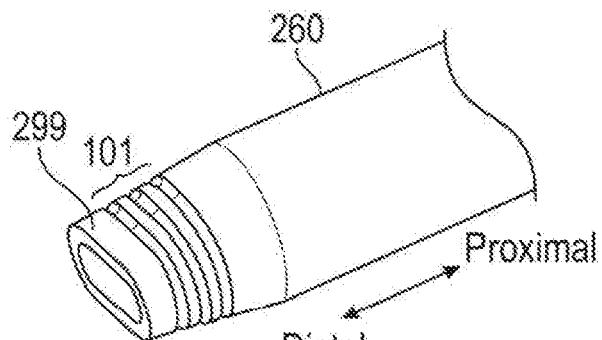
FIGS. 6A-6C are various views showing an example of a sleeve that can be included in an ophthalmic device.
Figure 6B:
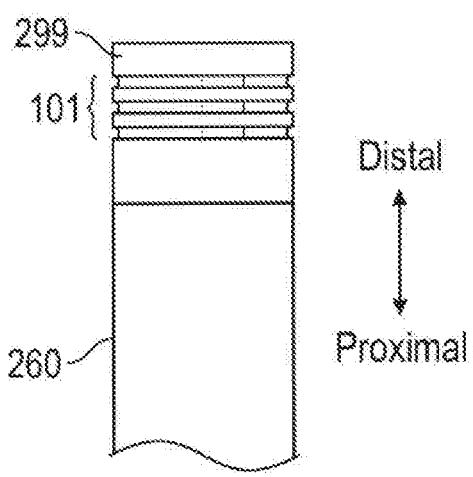
Figure 6C:
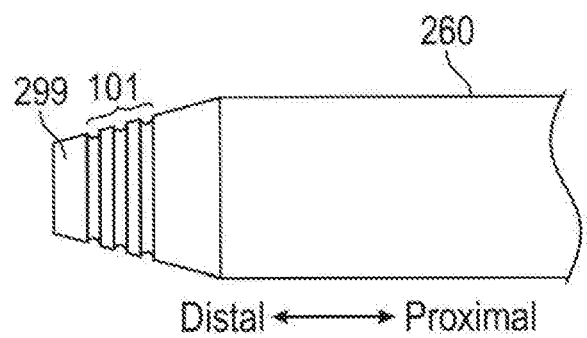

FIGS. 6A-6C are various views of a distal portion of an example of sleeve 260 including collar 299. FIG. 6A is a perspective view of the sleeve 260, FIG. 6B is a top view of the sleeve 260 as implemented in FIG. 6A, and FIG. 6C is a side view of the sleeve 260 as implemented in FIG. 6A. As shown for example in FIGS. 6A-6C, an outer surface of the collar 299 and outer surface of a distal portion of the sleeve 260 can further include grooves 101. The grooves 101 may enhance a suction effect when the sleeve 260 and collar 299 are retracted proximally by increasing a surface area of the outer surface of that contacts fluids, such as OVD or other surrounding fluids that can be disposed in the anterior chamber of the eye. The grooves 101 are shown in FIGS. 6A-6C as a plurality of circumferential grooves that extend around an outer circumference of the sleeve 260 and are disposed in a converging region of the collar 299 at a distal portion of the sleeve 260, but it is contemplated that the grooves 101 can be implemented as other types of surface area enhancing textures and/or positioned in other locations along an axial length of the sleeve.

Figure 7A:
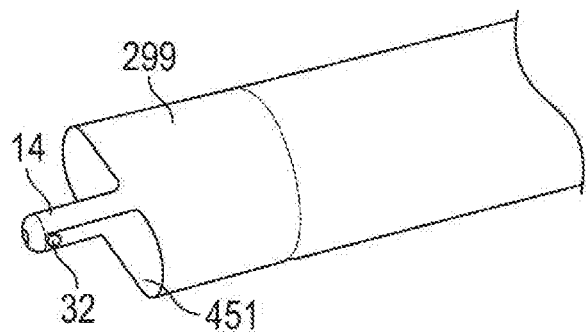
FIGS. 7A-7C are various views of an example of a cannula that can be included in an ophthalmic device.
Figure 7B:
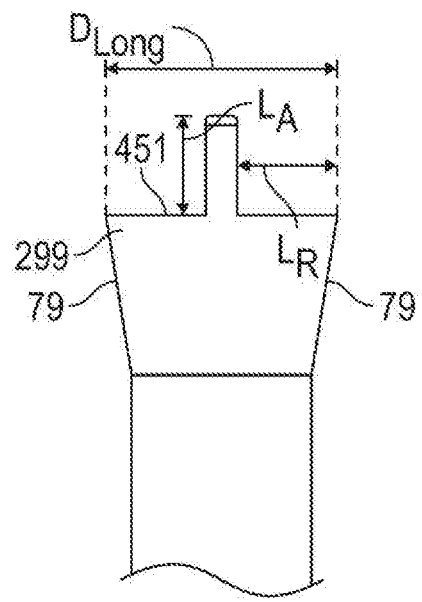
Figure 7C:
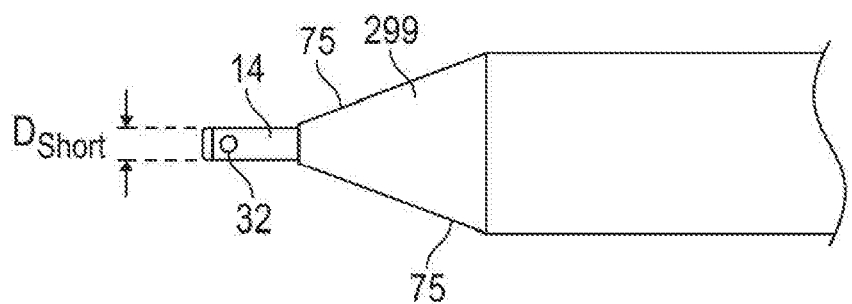

It is also contemplated, for example as shown in FIGS. 7A-7C, that the collar 299 can be fixedly coupled to the cannula 14. FIG. 7A is a perspective view of cannula 14, FIG. 7B is a top view of the cannula 14 as implemented in FIG. 7A, and FIG. 7C is a side view of cannula 14 as implemented in FIG. 7A.

In this example, an independently movable sleeve may be omitted from the ophthalmic device 10. For example, the collar 299 can be integrally formed as part of an outer portion of the cannula 14, or the collar 299 can be welded or otherwise fixedly attached to the cannula 14 so that the collar 299 moves together with the cannula 14. The fixedly coupled collar 299 can have an oblong cross-sectional shape or any of the other features described above with respect to the collar 299 when implemented on the sleeve. As shown for example in FIGS. 7A and 7B, a lip can be provided by a face of the collar 299 and protrude radially outward from a distal portion of cannula 14. The lip can thus provide a structure for interacting with tissue as described above. As shown for example in FIG. 7B, a radial length $L_R$ of lip can be approximately equal to an axial length $L_A$ of the protruding portion of the cannula 14, although it is contemplated that other dimensions may be suitably used. In this example, the lip length $L_R$ is defined by the distance between the radially outermost surface of the lip and the radially outermost surface of the axially protruding section of the cannula 14 from which the lip can extend. The cannula tip length $L_A$ is defined by the axial length from the lip (or from the face 451 or distal end of the collar 299) to the distal end of the cannula 14. The cannula 14 may have an increased diameter in a portion proximal to the collar 299 than in a portion distal to the collar 299. This may beneficially enhance rigidity or structural integrity of the cannula 14 across its working length, while permitting the distal end of the cannula 14 to be made sufficiently small in diameter for insertion into Schlemm's canal or another suitable target site of the patient. It is also contemplated that any of these dimensions or geometric features described with respect to the fixed collar shown in FIGS. 7A-7C can be suitably used in implementations where the collar is part of the sleeve 260 or otherwise movable with respect to the cannula 14 and disposed in a second configuration like that shown in FIG. 2B.

Figure 8:
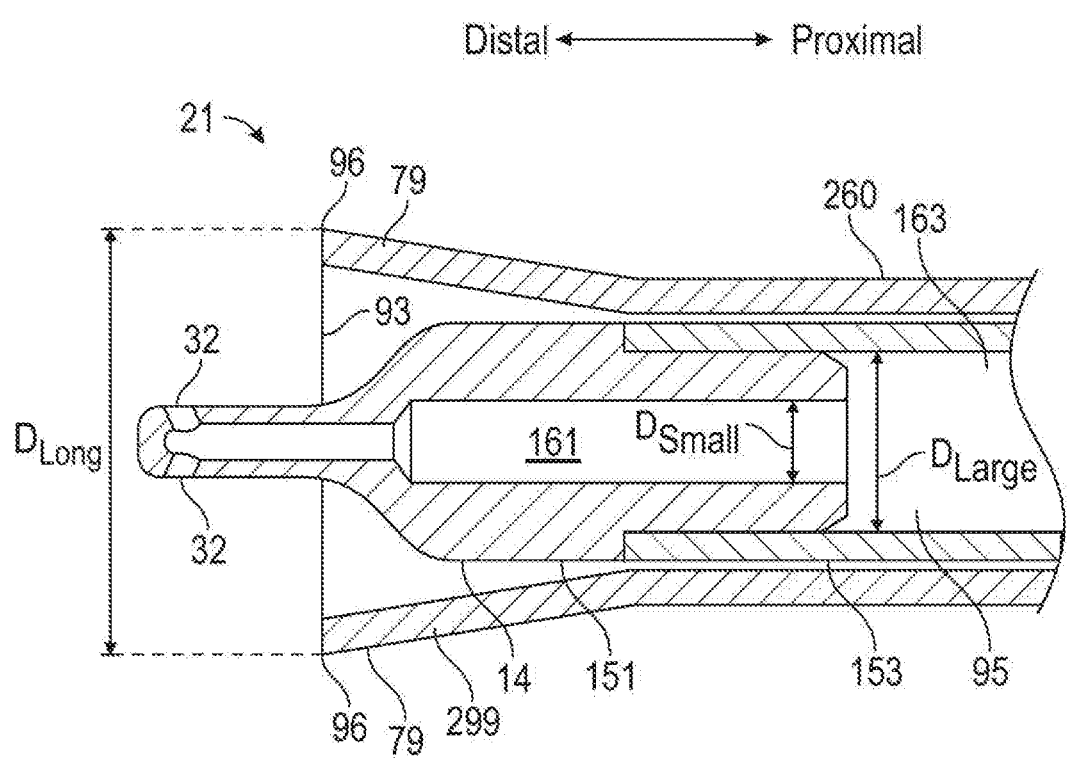
FIG. 8 is a longitudinal section view showing an example of a sleeve that can be included in an ophthalmic device.

FIG. 8 is a longitudinal section view showing a distal portion of an example of ocular component 21 that can be included in ophthalmic device 10. In the example shown in FIG. 8, the cannula 14 is shown in a protruding position relative to the sleeve 260 (e.g., in the second configuration like that shown in FIG. 2B). The cannula 14 is composed of a plurality of segments including a tip segment 151 and a proximal shaft segment 153. The tip segment 151 can be attached to the proximal shaft segment 153 by, for example, laser welding or any other suitable fastening mechanism. The tip segment 151 has an inner diameter $D_{SMALL}$ and the proximal shaft 153 has an inner diameter $D_{LARGE}$ that is greater than the inner diameter $D_{SMALL}$ of the tip segment 151. Accordingly, the lumen 95 extending through the cannula 14 is segmented to have a proximal portion 163 that is larger in diameter than the distal portion 161. This can, for example, reduce back pressure in the device, although implementations are also contemplated in which the cannula 14 is composed of a single piece or integral construction, and/or in which the lumen 96 has a substantially constant diameter through the cannula 14.

FIG. 8 also shows the collar 299 configured as shown in the example of FIGS. 5A-5C, in which the collar 299 is implemented at the distal end of the sleeve 260 so that a distal tip of the sleeve 260 has an oblong cross section with flared diverging outer surfaces 79 on opposing sides of the sleeve 260. As shown in the example of FIG. 8, the one or more orifices 32 can include a pair of orifices on opposing sides of the cannula 14 (e.g., oriented approximately 180 degrees apart from one another about the circumference of the cannula 14). The pair of opposing orifices can be aligned along the long axis 85 of the distal tip (aligned along the long axis of the oblong cross section of the collar 299) so that the orifices 32 face the short sides 96 of the sleeve distal end and face the diverging outer surfaces 79. This can, for example, allow the flared or diverging surfaces to serve as an indicator for bringing the orifices of the cannula 14 into the Schlemm's canal with an orientation that points the injected fluid towards the direction of extent of the canal. Although shown in an implementation in which the collar 299 is fixedly coupled to a movable sleeve 260, it is also contemplated that this orientation of the orifices 32 can be applied to implementations in which the collar 299 is fixed to the cannula 14 like in the example of FIGS. 7A-7C.

Figure 9A:
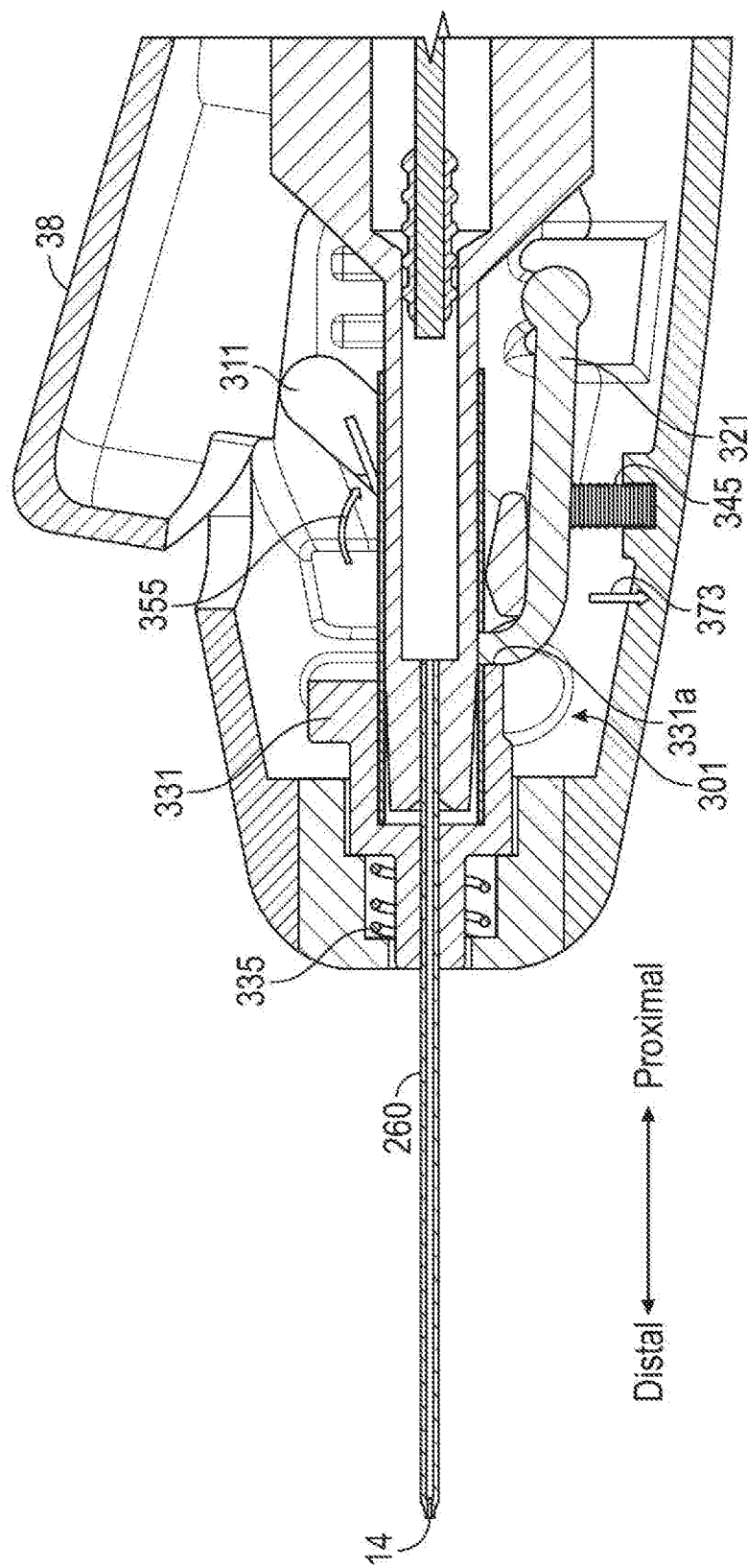
FIGS. 9A-9C are cross-sectional side views showing an example of a mechanism that can be configured to retract a sleeve in an ophthalmic device.
Figure 9B:
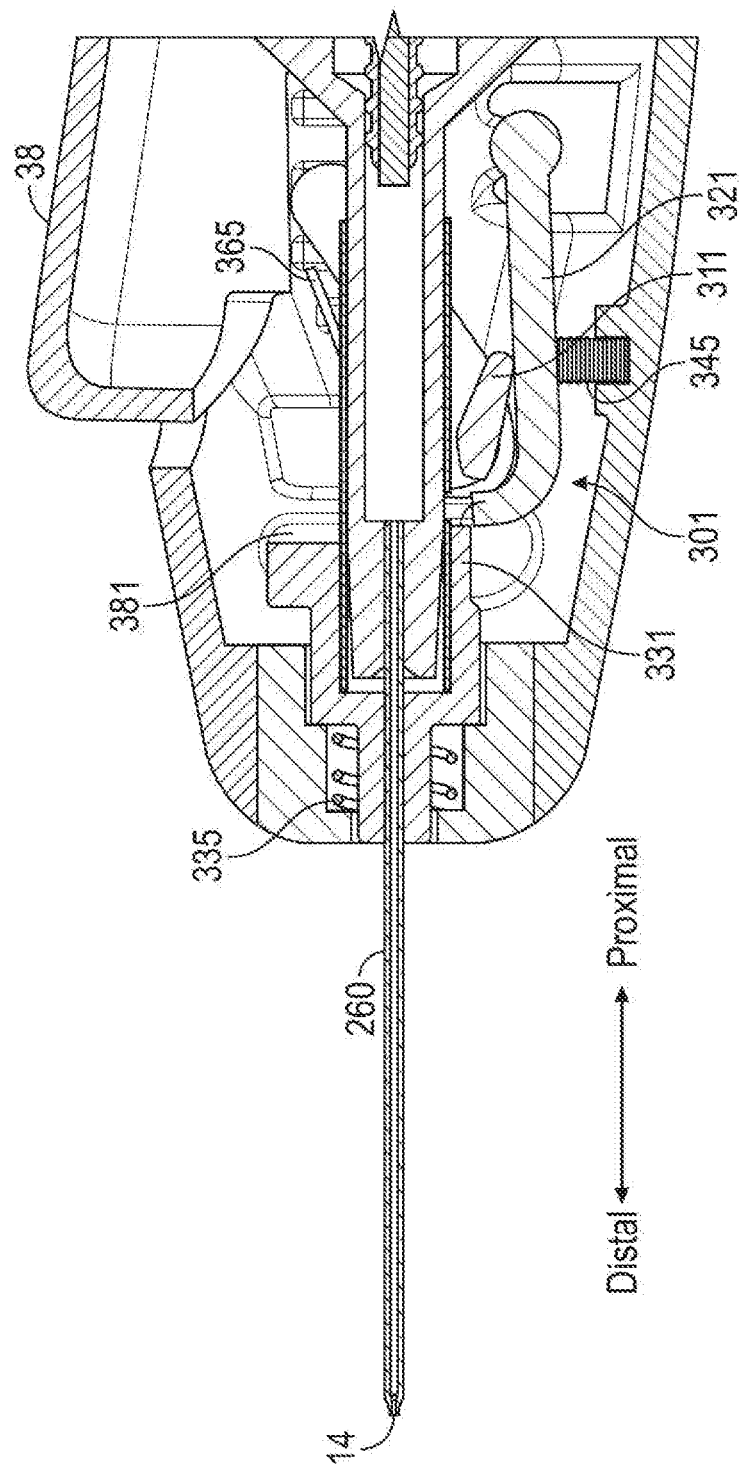
Figure 9C:
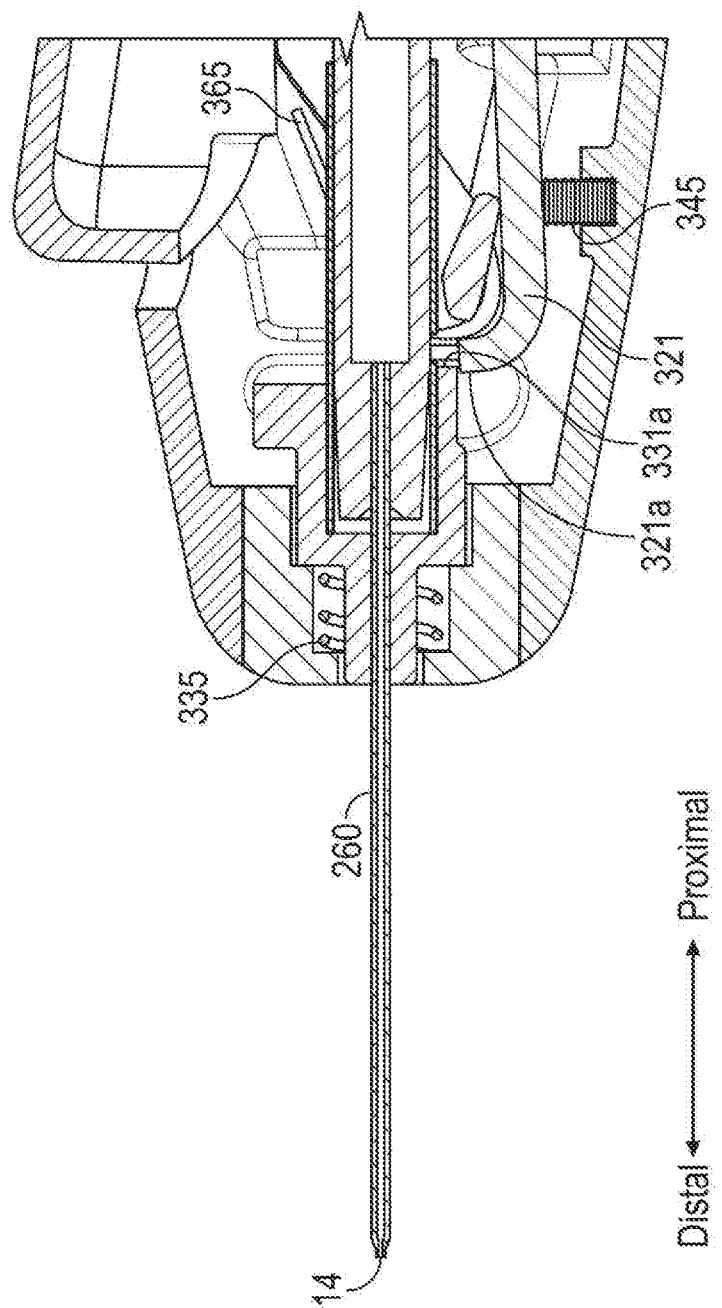

FIGS. 9A-9C are various views showing an example of an internal mechanism 301 disposed in the ophthalmic device 10 and utilized to retract sleeve 260. The internal mechanism 301 can, for example, be disposed in an internal volume of the handle 12 and coupled to the actuator 38.

FIG. 9A shows the internal mechanism 301 in an initial loaded state, FIG. 9B shows the internal mechanism 301 in an intermediate state (e.g., as the actuator 38 is pressed), and FIG. 9C shows the internal mechanism 301 in a released state during or after retraction of the sleeve 260. The internal mechanism 301 shown in FIGS. 9A-9C utilizes a cam and follower system to retract sleeve 260 in a proximal direction relative to the cannula 14 and relative to the handle 12. More particularly, the internal mechanism 301 includes a cam 311 (e.g., rocker) coupled to a catch 321 and a slidable spring-loaded follower 331. The follower 331 can be fixedly coupled to the sleeve 260 so that the sleeve 260 moves together with the follower 331. The catch 321 is configured to hold the follower 331 in a distal position, and the cam 311 is configured to move the catch 321 to release the follower 331 in the proximal direction. The cam 311 is coupled to the actuator 38 to permit the cam 311 to be moved or actuated by pressing the actuator 38.

In FIG. 9A, the internal mechanism 301 is shown in an initial state. In this state, the follower 331 (and the sleeve 260) are in a distal position. The catch 321 is in a first position in which it holds the follower 331 in the distal position by, for example, abutting a proximal surface 331a of the follower 331 to prevent or restrict proximal movement of the follower 331. While the catch 321 is in the first position and the follower 331 is in the distal position, a spring 335 applies a spring force to the follower 331 in the proximal direction. The spring 335 is shown in FIGS. 9A-9C as an axial compression spring, but it will be appreciated that a variety of other springs can be suitably used. The actuator 38 coupled to the cam 311 is in an un-pressed position (e.g., an upper position) when the internal mechanism 301 is in the initial state. Application of a user force to the actuator 38 can urge rotational movement of the cam 311 in a first rotational direction 355 about cam pivot point 343. As the cam 311 rotates in the first rotational direction 355, the cam 311 rotates against the catch 321 to urge movement of the catch 321, for example, to flex in a direction 373 away from the first position of the catch and towards a second position of the catch. The flex (e.g., downward movement) of the catch 321 may have to overcome a biasing force of a biasing spring 345.

In FIG. 9B, the internal mechanism 301 is shown in an intermediate state as the above forces are being applied. As shown in FIG. 9B, a gap 381 can be formed between the cam 311 and the follower 331 upon rotation of the cam 311 in the first rotational direction 355. For example, as the cam 311 rotates against the catch 321, the catch 321 can continue to hold the follower 331 in a distal position while the cam 311 rotates away from the follower 331 in the first rotational direction 355. The gap 381 can provide a clearance for the follower 331, together with the sleeve 260, to freely move so that potential energy held in the spring 335 can cause a quick and sharp snapping motion upon release of the follower 331 by the catch 321. Further, the downward flex of the catch 321 compresses the biasing spring 345 and increases the potential energy held in the biasing spring 345. Also, the cam 311 may be coupled to a torsion spring 365 and the rotation of the cam 311 in the first rotational direction 355 causes the potential energy held in the torsion spring 365 to increase.

In FIG. 9C, the internal mechanism 301 is shown in a retracted or retracting state in which the follower 331 is released by the catch 321. As shown in FIG. 9C, upon sufficient rotation of the cam 311 against the catch 321, the cam 311 can release the follower 331 by, for example, moving the catch 321 to a second position in which the catch 321 releases the follower 331 by, for example, removing a restriction with which a distal surface 321a of the catch 321 abuts against the proximal surface 331a of the follower 331. Upon release of the follower, potential energy stored in the spring 335 is released to urge proximal motion of the follower 331 (and thus the sleeve 260) in the proximal direction. The follower 331 can move freely through the gap 381 to a proximal position until it is stopped by a restriction. For example, the proximal motion of the follower 331 can terminate upon the follower 331 abutting the cam 311, upon abutting a stop included in a housing of the handle 12, and/or upon abutting a stop included on the catch 321. The surface that provides a stop for the follower 331 can, for example, be relatively rigid or can include a cushion or energy absorbing member so as to soften an impact and prevent shocks from transmitting through the device and to a surgeon's hand.

In FIG. 9C, the catch 321 is shown in a second position (released position). The catch 321 can be biased by the biasing spring 345 to the first position (abutting position shown in FIG. 9A) so as to permit the internal mechanism 301 to be reset to the initial state upon release of the actuator 38 by a user. For example, upon release of the actuator 38, a biasing force from the torsion spring 365 may urge rotational movement of the cam 311 in a second rotational direction opposite to the first rotational direction 355, and the cam 311 may urge the follower 331 in the distal direction (e.g., the follower 331 may retract) so as to move the follower 331 from the follower proximal position to the follower distal position to reload the spring 335. As the follower 331 moves distally in this manner, the biasing spring 345 urges the catch 321 to return to the first position where it abuts the follower 331 to hold the follower 331 in the distal position. The internal mechanism 301 can then be operated again in a similar fashion for one or more repeated sleeve 260 retractions.

Figure 10A:
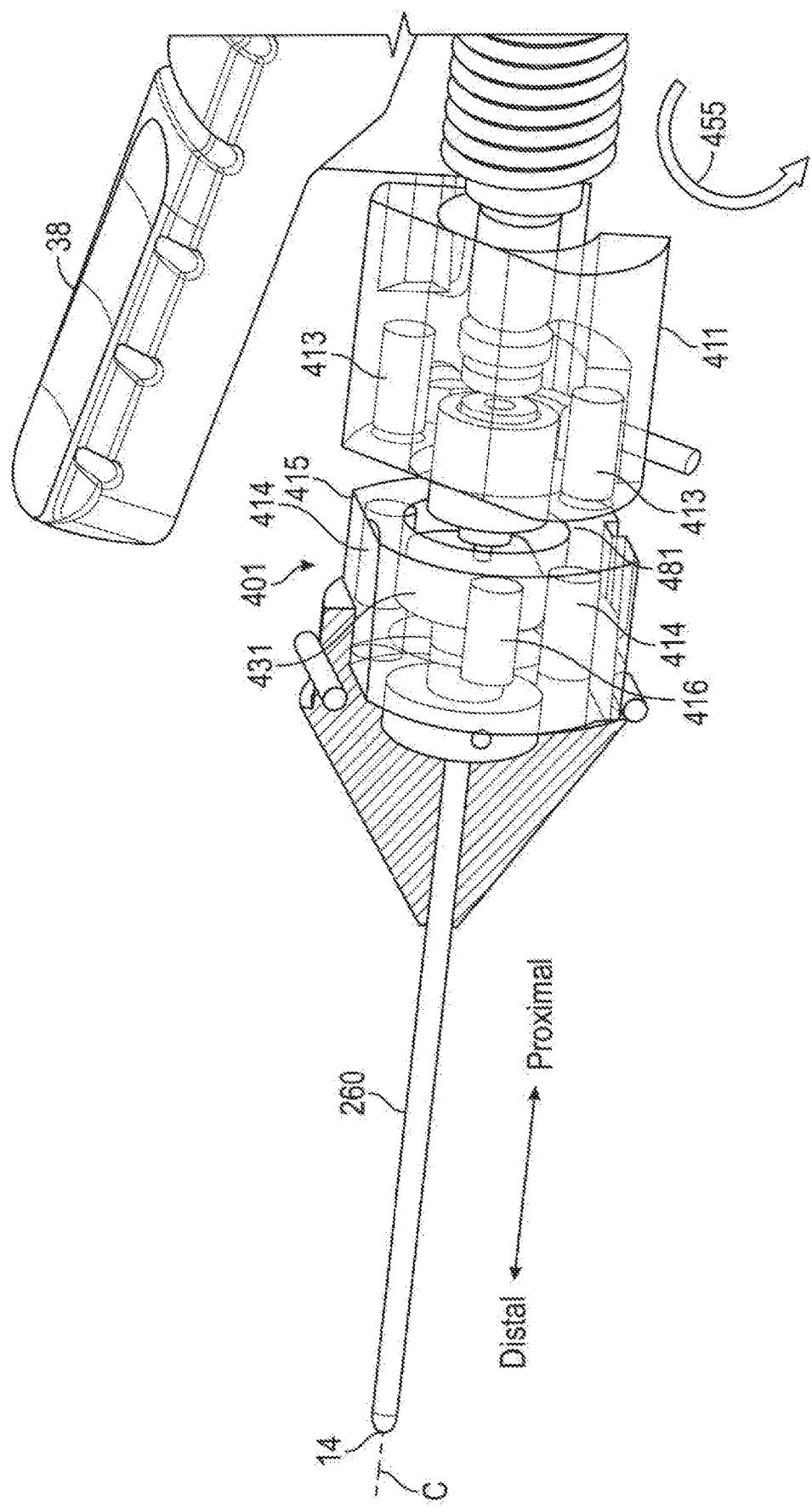
FIGS. 10A-10C are perspective views showing an example of a mechanism that can be configured to retract a sleeve in an ophthalmic device.
Figure 10B:
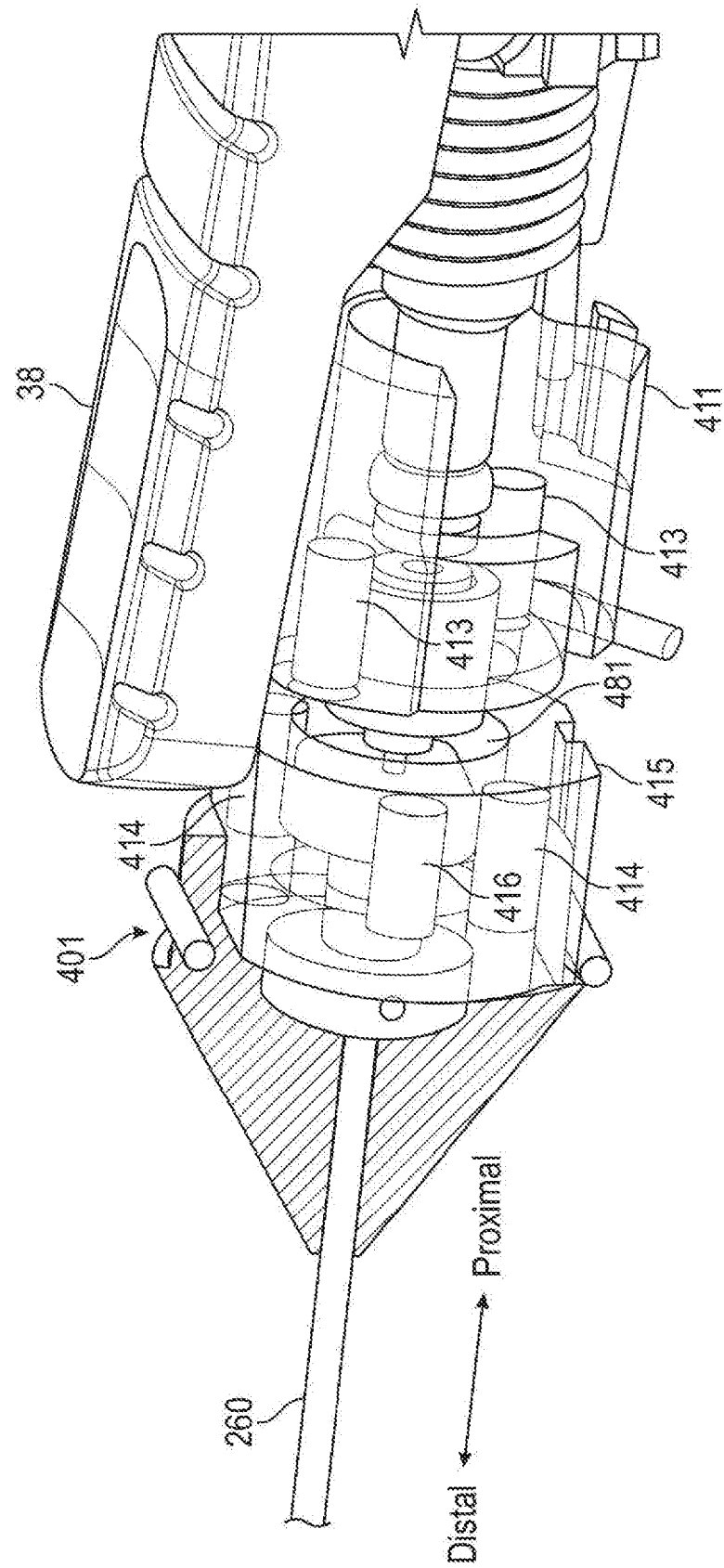
Figure 10C:
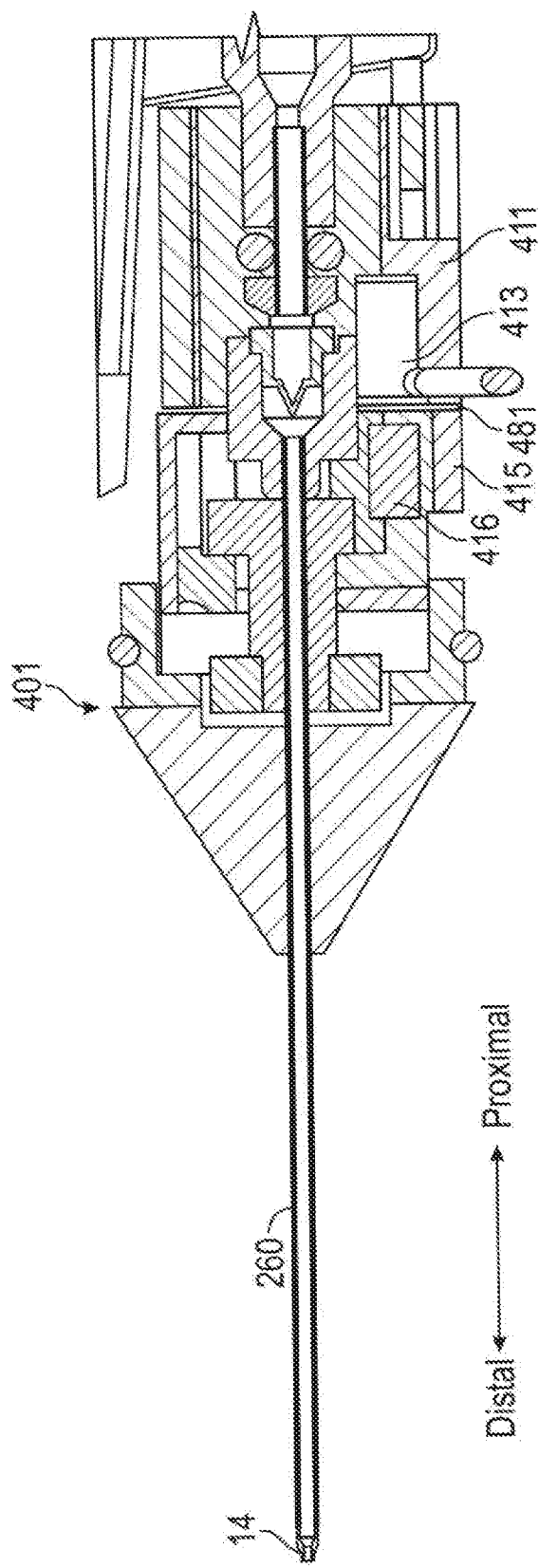

FIGS. 10A-10C are various views showing an example of an internal mechanism 401 disposed in the ophthalmic device 10 and utilized to retract sleeve 260. The internal mechanism 401 can, for example, be disposed in an internal volume of the handle 12 and coupled to the actuator 38.

FIG. 10A shows the internal mechanism 401 in an initial loaded state, FIG. 10B shows the internal mechanism 401 in an intermediate state (e.g., as the actuator 38 is pressed), and FIG. 10C shows the internal mechanism 401 in a released state during or after retraction of the sleeve 260. The internal mechanism 401 shown in FIGS. 10A-10C utilizes a magnetic assembly to retract sleeve 260 in a proximal direction relative to the cannula 14 and relative to the handle 12. More particularly, the internal mechanism 401 includes a rotatable housing 411 having one or more magnets 413 disposed within the rotatable housing 411. For example, as shown in FIG. 10A, the rotatable housing 411 has two magnets 413 disposed 180 degrees apart. The rotatable housing 411 is configured to rotate about the central longitudinal axis C. The internal mechanism 401 also includes a slidable housing 415 having one or more magnets 414, 416 disposed within the slidable housing 415. For example, as shown in FIG. 10A, the slidable housing 415 has four magnets 414, 416 arranged in two sets, one set of magnets 416 configured to attract and one set of magnets 414 configure to repel the magnets 413 in the rotatable housing 411. Here, each set of magnets 414, 416 is disposed 180 degrees apart. The internal mechanism 401 further includes a slidable follower 431. The follower 431 can be fixedly coupled to the sleeve 260 so that the sleeve 260 moves together with the follower 431. The slidable housing 415 is configured to hold the follower 431 in a distal position, and the rotatable housing 411 is configured to align the attracting magnets 416 with the magnets 413 to release the follower 431 in the proximal direction. The rotatable housing 411 is coupled to the actuator 38 to permit the rotatable housing 411 to be moved or actuated by pressing the actuator 38.

In FIG. 10A, the internal mechanism 401 is shown in an initial state. In this state, the follower 431 (and the sleeve 260) are in a distal position. The slidable housing 415 is in a first position in which it holds the follower 431 in the distal position by, for example, engaging the follower 431 to prevent or restrict proximal movement of the follower 431. The slidable housing 415 is held in the first position when the rotatable housing 411 is aligned such that the magnets 413 are aligned with the opposing magnets 414, which applies a repelling force to the slidable housing 415 in the distal direction. The actuator 38 coupled to the rotatable housing 411 is in an un-pressed position (e.g., an upper position) when the internal mechanism 401 is in the initial state. Application of a user force to the actuator 38 can urge rotational movement of the rotatable housing 411 in a first rotational direction 455 about the central longitudinal axis C. As the rotatable housing 411 rotates in the first rotational direction 455, the magnets 413 move out of alignment with the opposing magnets 414 and the repelling force lessens.

In FIG. 10B, the internal mechanism 401 is shown in an intermediate state as the above forces are being applied. As shown in FIGS. 10A and 10B, a gap 481 exists between the rotatable housing 411 and the slidable housing 415 in the initial and intermediate states. The gap 481 is maintained by the repelling or opposing force of the magnets 413 and the magnets 414 in the initial state. In the intermediate state, the gap 481 will remain the same size once the magnets 413 are moved out of alignment with the magnets 414 until another force is placed on the slidable housing 415.

In FIG. 10C, the internal mechanism 401 is shown in a retracted state in which the slidable housing 415 and the follower 431 have moved in a proximal direction towards the rotatable housing 411. As shown in FIG. 10C, upon sufficient rotation of the rotatable housing 411, the magnets 413 become aligned with the attracting magnets 416, which causes an attractive force on the slidable housing 415. The slidable housing 415 engaged with the follower 431 can move freely through the gap 381 to a proximal position until it is stopped by a restriction. For example, the proximal motion of the follower 431 can terminate upon the follower 431 abutting a portion of the rotatable housing 411, upon abutting a stop included in a housing of the handle 12, and/or upon the slidable housing 415 abutting the rotatable housing 411. The surface that provides a stop for the follower 431 and/or the slidable housing 415 can, for example, be relatively rigid or can include a cushion or energy absorbing member so as to soften an impact and prevent shocks from transmitting through the device and to a surgeon's hand.

In FIG. 10C, the slidable housing 415 and the rotatable housing 411 are shown in an attracted position. The slidable housing 415 can be urged by the magnets 414 to opposed position (distal position shown in FIG. 10A) so as to permit the internal mechanism 401 to be reset to the initial state upon release of the actuator 38 by a user. For example, upon release of the actuator 38, a trigger upstroke may urge rotational movement of the rotational housing 411 in a second rotational direction opposite to the first rotational direction 455 until the magnets 413 are aligned with the repelling magnets 414. This causes a repelling force that moves the slidable housing 415 and the follower 431 from the follower proximal position to the follower distal position. The slidable housing 415 moves distally in this manner until the slidable housing 415 or the follower 431 abuts a stop, wherein the opposing or repelling force from the magnets 413, 414 holds the follower 431 in the distal position. The internal mechanism 401 can then be operated again in a similar fashion for one or more repeated sleeve 260 retractions.

The internal mechanism 401 may be configured in particular ways. For example, the rotatable housing 411 and/or the slidable housing 415 may have any number of magnets 413, 414, 416. As another example, the rotatable housing 411 may be configured to rotate any desired amount, such as to rotate 45 degrees in the first rotational direction 455 and to rotate back 45 degrees in the second rotational direction.

FIGS. 11A-11D are various views showing an example of an internal mechanism 501 disposed in the ophthalmic device 10 and utilized to retract sleeve 260. The internal mechanism 501 can, for example, be disposed in an internal volume of the handle 12 and coupled to the actuator 38.

Figure 11A:
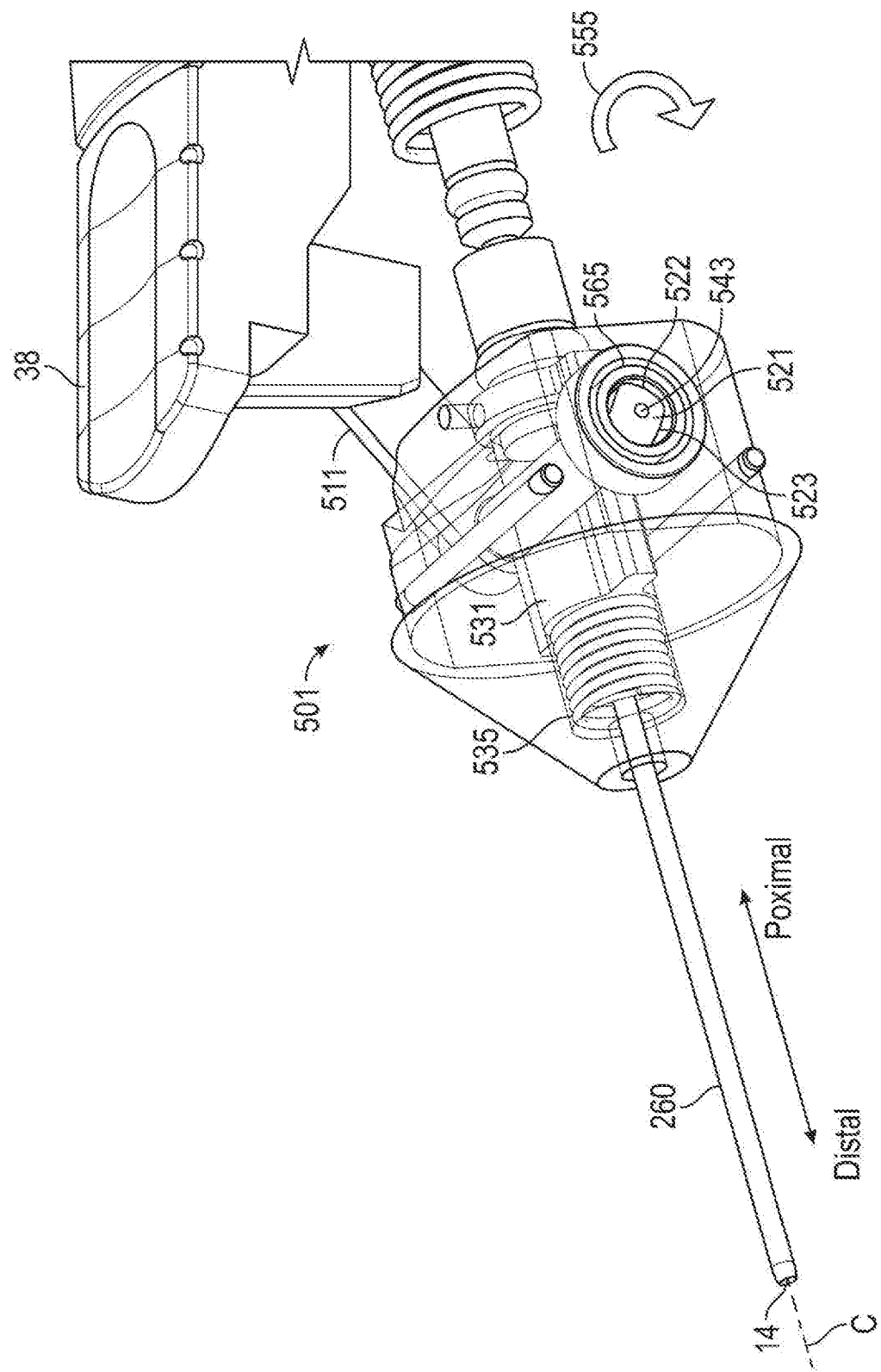
FIGS. 11A-11D are perspective and cross-sectional side views showing an example of a mechanism that can be configured to retract a sleeve in an ophthalmic device.
Figure 11B:
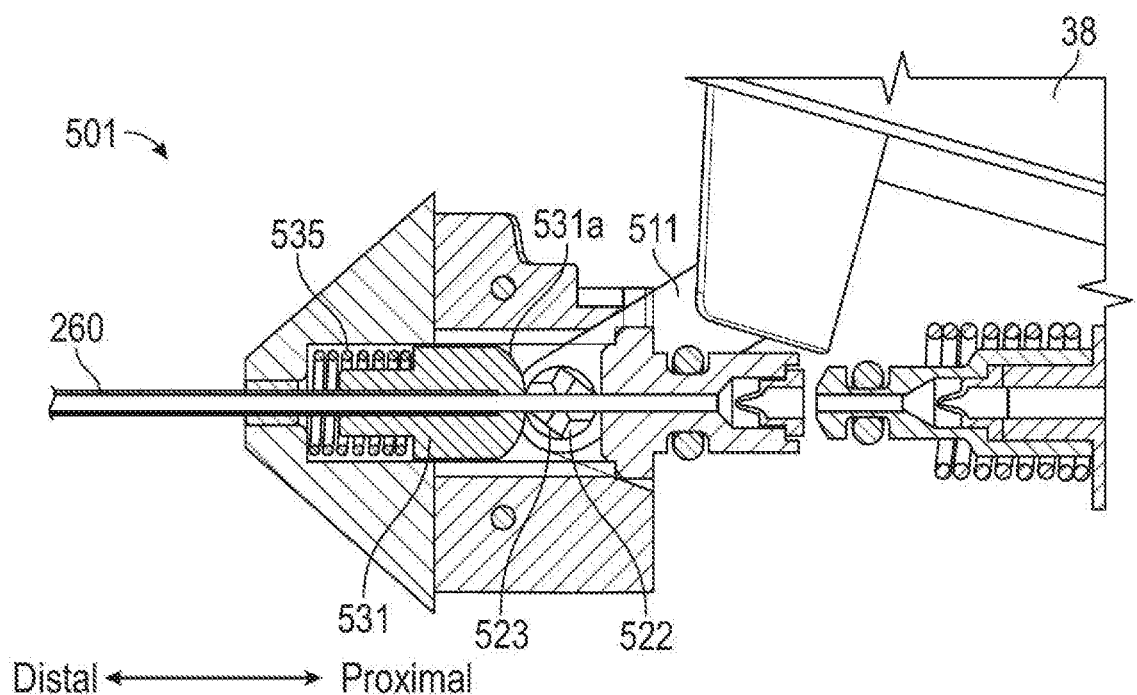
Figure 11C:
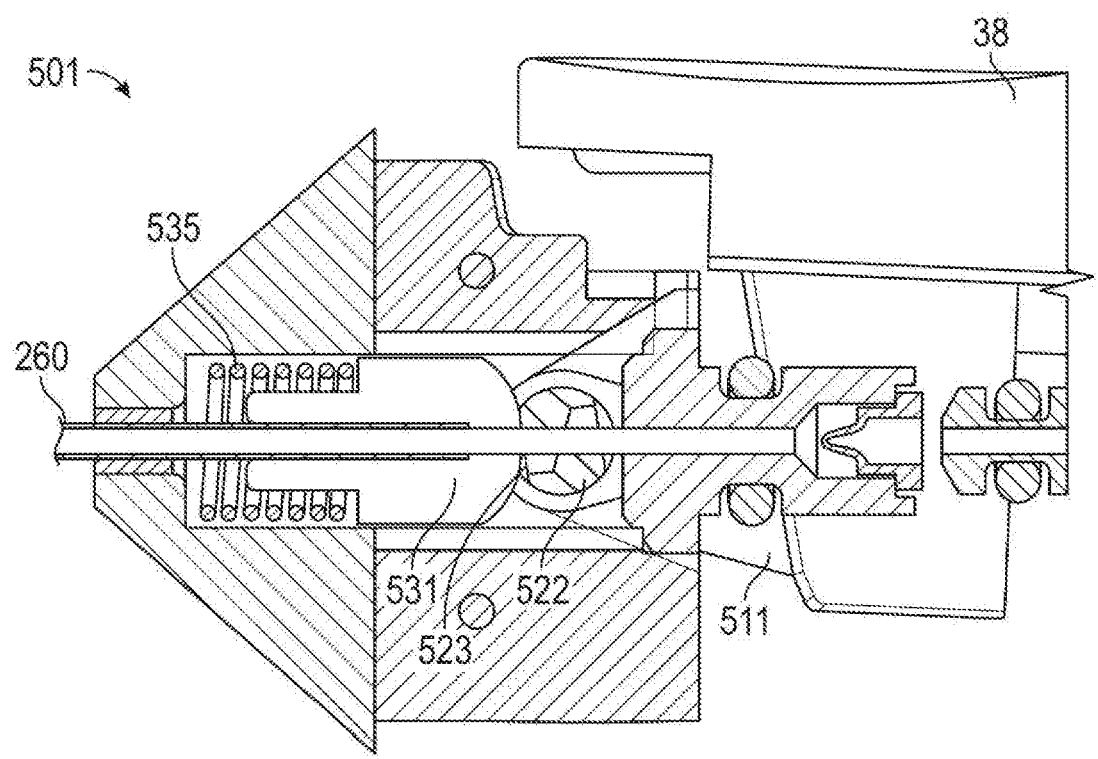
Figure 11D:
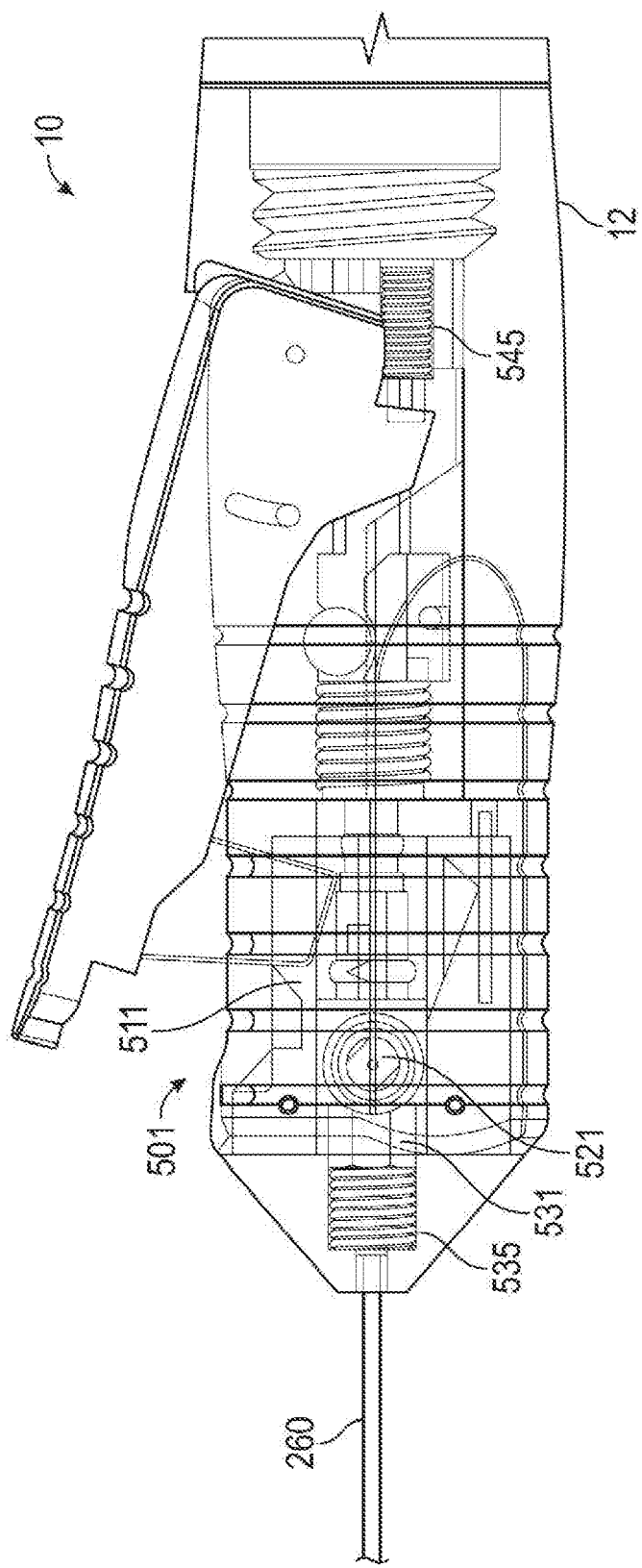

FIGS. 11A and 11B show the internal mechanism 501 in an initial loaded state, FIG. 11C shows the internal mechanism 501 in an intermediate state (e.g., as the actuator 38 is pressed), and FIG. 11D shows the internal mechanism 501 in a reset state after retraction of the sleeve 260. The internal mechanism 701 shown in FIGS. 11A-11D utilizes a dowel pin assembly to retract sleeve 260 in a proximal direction relative to the cannula 14 and relative to the handle 12. More particularly, the internal mechanism 501 includes an arm 511 (e.g., rotating lever) coupled to a dowel pin 521 and a slidable spring-loaded follower 531. The follower 531 can be fixedly coupled to the sleeve 260 so that the sleeve 260 moves together with the follower 531. The follower 531 may always be in contact with the dowel pin 521.

The dowel pin 521 may have two rounded portions 522 and two flat portions 523 (e.g., double D configuration) and may be disposed perpendicularly to the central longitudinal axis C of the sleeve 260. The dowel pin 521 is configured to hold the follower 531 in a distal position, and the arm 511 is configured to move (e.g., rotate) the dowel pin 521 to release the follower 531 in the proximal direction. The arm 511 is coupled to the actuator 38 to permit the arm 511 to be moved or actuated by pressing the actuator 38. A roller bearing 565 may be coupled to the opposite side of the dowel pin 521 as the arm 511. The cannula 14 may be configured to pass through an opening in the dowel pin 521 to prevent the dowel pin 521 from contacting the cannula 14 during rotation of the dowel pin 521, thus avoiding asymmetric loading that could cause jamming of the dowel pin 521. The depth of the dowel pin 521 abutting the follower 531 may change from 94 thousandths of an inch to 80 thousandths of an inch in 15 degrees of rotation, thus providing for a sleeve 260 retraction of 14 thousandths of an inch.

In FIGS. 11A and 11B, the internal mechanism 501 is shown in an initial state. In this state, the follower 531 (and the sleeve 260) are in a distal position. The dowel pin 521 is in a first position in which it holds the follower 531 in the distal position by, for example, one of the rounded portions 522 abutting a proximal surface 531a of the follower 531 to prevent or restrict proximal movement of the follower 531. While the dowel pin 521 is in the first position and the follower 531 is in the distal position, a preload spring 535 applies a spring force to the follower 531 in the proximal direction. The preload spring 535 is shown in FIGS. 11A-11D as an axial compression spring, but it will be appreciated that a variety of other springs can be suitably used. The actuator 38 coupled to the arm 511 is in an un-pressed position (e.g., an upper position) when the internal mechanism 501 is in the initial state. Application of a user force to the actuator 38 can urge rotational movement of the arm 511 in a first rotational direction 555 about pivot point 543. As the arm 511 rotates in the first rotational direction 555, the arm 511 rotates the dowel pin 521 to urge movement of the dowel pin 521, for example, to rotate in the first rotational direction 555.

In FIG. 11C, the internal mechanism 501 is shown in an intermediate state as the above forces are being applied. When the dowel pin 521 rotates so that one of the flat portions 523 begins to contact the proximal surface 531a of the follower 531, then the force of the preload spring 535 causes the follower 531 to quickly move (e.g., snap) in the proximal direction, which causes the dowel pin 521 rotate further (e.g., spin) in the first rotational direction 555. The proximal movement of the follower 531 causes the sleeve 260 to move in the proximal direction, thereby retracting the sleeve 260 from the distal end of the cannula 14.

In FIG. 11D, the internal mechanism 501 is shown in a reset state. The internal mechanism 501 is reset when the pressing force on the actuator 38 is released (e.g., finger removed from actuator) and a reset spring 545 coupled to the actuator 38 causes the actuator 38 to lift back to the initial position. As the actuator 38 lifts, the arm 511 rotates (e.g., lifts up), thus causing the dowel pin 521 to rotate so that one of the rounded portions 522 abuts the follower 531. This movement forces the follower 531 and the sleeve 260 to move back in the distal direction, thus resetting the internal mechanism 501 for another cycle.

FIGS. 12A-12E are various views showing an example of an internal mechanism 601 disposed in the ophthalmic device 10 and utilized to retract sleeve 260. The internal mechanism 601 can, for example, be disposed in an internal volume of the handle 12 and coupled to the actuator 38.

Figure 12A:
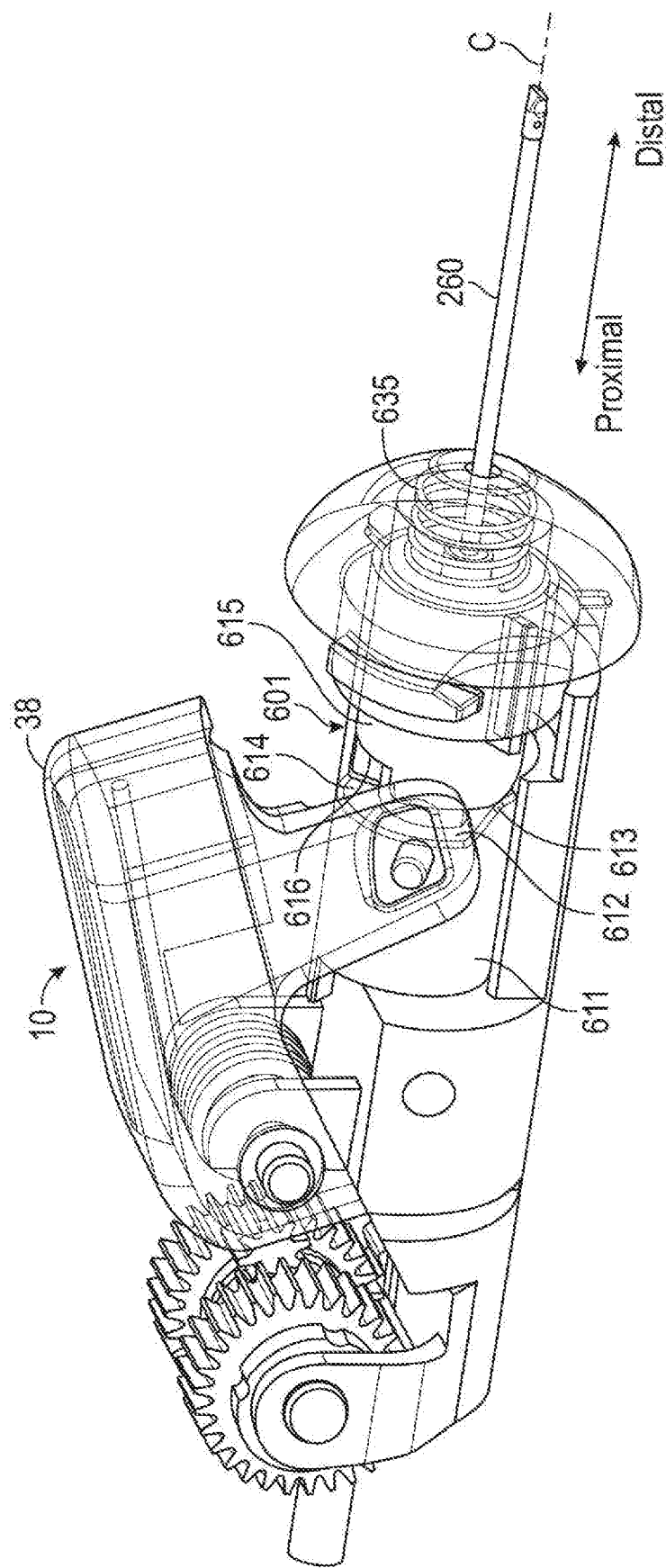
Figure 12B:
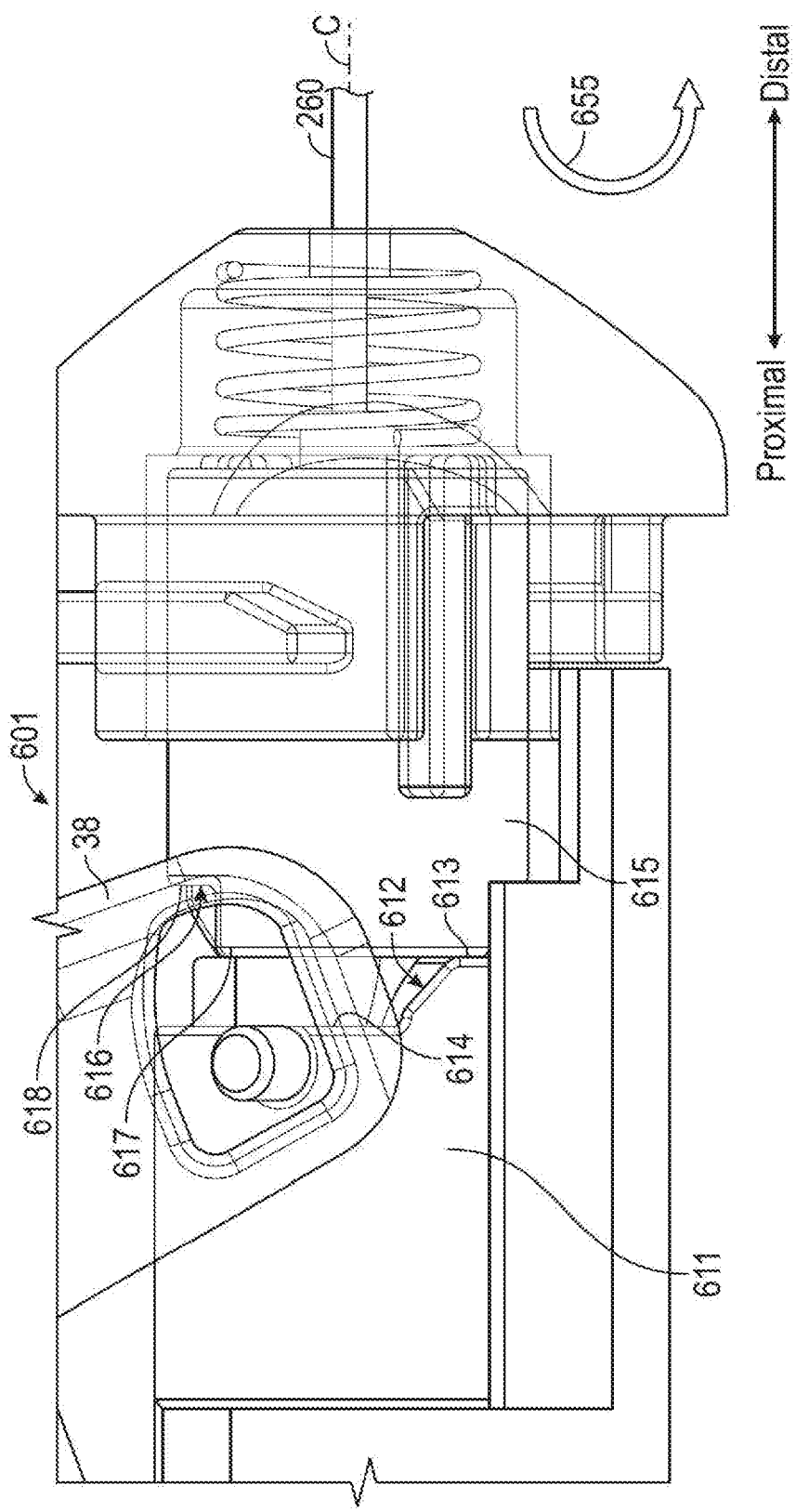
Figure 12E:
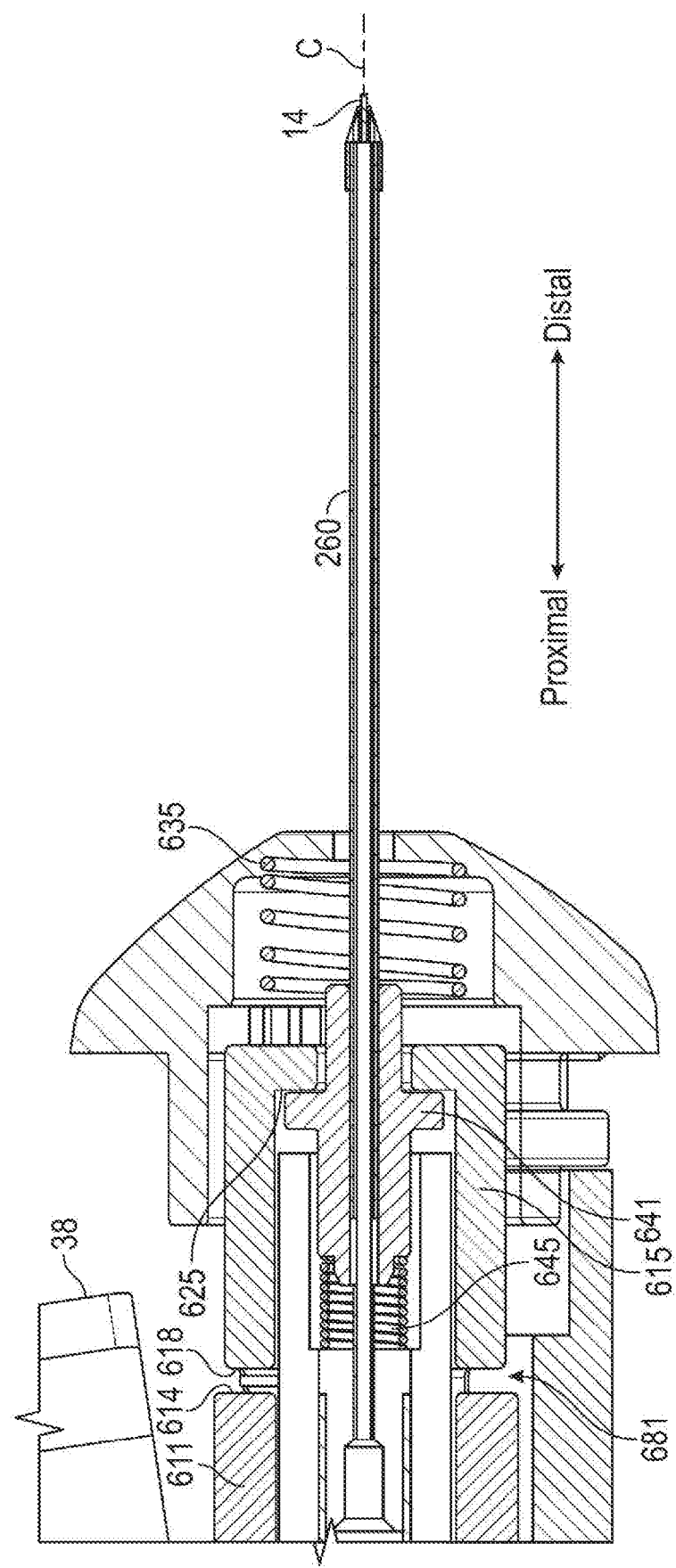

FIGS. 12A-12C show the internal mechanism 601 in an initial loaded state and FIGS. 12D and 12E show the internal mechanism 601 in a released state (e.g., after the actuator 38 is pressed) during or after retraction of the sleeve 260. The internal mechanism 601 shown in FIGS. 12A-12E utilizes a hills and valleys assembly to retract sleeve 260 in a proximal direction relative to the cannula 14 and relative to the handle 12. More particularly, the internal mechanism 601 includes a rotatable housing 611 having a varied cam surface 612 on a distal end of the rotatable housing 611. The varied cam surface 612 may have hill (e.g., elevated) portions 613 and valley (e.g., recessed) portions 614. The rotatable housing 611 is configured to rotate about the central longitudinal axis C. The internal mechanism 601 also includes a slidable housing 615 having a varied cam surface 616 on a proximal end of the slidable housing 615. The varied cam surface 616 may have hill portions 617 and valley portions 618. The internal mechanism 601 further includes a slidable follower 631. The follower 631 can be fixedly coupled to the sleeve 260 so that the sleeve 260 moves together with the follower 631. The slidable housing 615 is configured to hold the follower 631 in a distal position, and the rotatable housing 611 is configured to align a hill portion 613 with a hill portion 617 to move and/or hold the follower 631 in the proximal direction. The rotatable housing 611 is coupled to the actuator 38 to permit the rotatable housing 611 to be moved or actuated by pressing the actuator 38.

In FIGS. 12A-12C, the internal mechanism 601 is shown in an initial state. In this state, the follower 631 (and the sleeve 260) are in a distal position. The slidable housing 615 is in a first position in which it is engaged and pushed against a preload spring 635. In the first position, the slidable housing 615 may not be engaged with the follower 631 and thus may allow proximal movement of the follower 631. The slidable housing 615 is held in the first position when the rotatable housing 611 is aligned such that a hill portion 613 is aligned with a hill portion 617, which holds the slidable housing 615 in the distal direction. The actuator 38 coupled to the rotatable housing 611 is in an un-pressed position (e.g., an upper position) when the internal mechanism 601 is in the initial state. Application of a user force to the actuator 38 can urge rotational movement of the rotatable housing 611 in a first rotational direction 655 about the central longitudinal axis C, such as by 45 degrees, for example. As the rotatable housing 611 rotates in the first rotational direction 655, the hill portion 617 moves out of alignment with the opposing hill portion 613 and into the valley portion 614.

As shown in FIG. 12C, a gap 681 may be disposed between the rotatable housing 611 and the slidable housing 615 in the initial state. The gap 681 is maintained by the opposing hill portions 613, 617 in the initial state. A gap 691 may also be disposed between an internal surface 625 of the slidable housing 615 and a stop 641 of the follower 631. The gaps 681, 691 will each remain at its widest in the initial state until the actuator 38 is pressed and the rotatable housing 611 begins to rotate.

In FIGS. 12D and 12E, the internal mechanism 601 is shown in a retracted state in which the slidable housing 615 and the follower 631 have moved in a proximal direction towards the rotatable housing 611. As shown in FIGS. 12D and 12E, upon rotation of the rotatable housing 611, the hill portion 613 slides down from the hill portion 617 into the valley portion 618 on the slidable housing 615. Similarly, the hill portion 617 of the slidable housing 615 becomes rotatably aligned with the valley portion 614 of the rotatable housing 611. The slidable housing 615 may move freely through the gap 681 (e.g., the gap 681 shrinks) until the internal surface 625 of the slidable housing 615 engages the stop 641 of the follower 631 (e.g., the gap 691 is eliminated). The slidable housing 615 and the engaged follower 631 may continue to move to a proximal position due to force from the preload spring 635 until stopped by a restriction. For example, the proximal motion of the follower 631 can terminate upon the hill portions 613, 617 abutting the valley portions 614, 618, upon the slidable housing 615 and/or the follower 631 abutting a stop included in a housing of the handle 12, and/or upon the follower 631 compressing a damper spring 645. The surface that provides a stop for the follower 631 and/or the slidable housing 615 can, for example, be relatively rigid or can include a cushion or energy absorbing member (e.g., damper spring 645) so as to soften an impact and prevent shocks from transmitting through the device and to a surgeon's hand.

In the retracted state shown in FIGS. 12D and 12E, the movement of the follower 631 in the proximal direction causes the sleeve 260 to retract and expose a distal portion of the cannula 14. The actuator 38 can be biased by a torsion spring 665 to the initial position so as to permit the internal mechanism 601 to be reset to the initial state upon release of the actuator 38 by a user. For example, upon release of the actuator 38, a biasing force from the torsion spring 665 may urge rotational movement of the rotatable housing 611 in a second rotational direction opposite to the first rotational direction 655, such as back 45 degrees, for example. The hill portions 613, 617 may slide up out of the valley portions 614, 618 and urge the slidable housing 615 in the distal direction so as to move the slidable housing 615 from the proximal position of the release state to the distal position of the initial state to reload the preload spring 635. As the slidable housing 615 moves in the distal direction, the follower 331 moves distally as well due to the force of the damper spring 645. The force of the damper spring 645 may be such that the stop 641 of the follower 631 bounces off of the internal surface 625 of the slidable housing 615 to create the gap 691. As another example, the follower 631 may be urged in the distal direction without the stop 641 bouncing off of the internal surface 625 (e.g., the slidable housing 615 moves further in the distal direction than does the follower 631). When the slidable housing 615 is in the initial position, the internal mechanism 601 can then be operated again in a similar fashion for one or more repeated sleeve 260 retractions.

The internal mechanism 601 may be configured to cause a hammer impact effect when the actuator 38 is pressed and the preload spring 635 causes the slidable housing 615 to snap or accelerate through the gap 681 in the proximal direction. In particular, the snap acceleration of the slidable housing 615 causes the internal surface 625 to impact the stop 641 of the follower 631 with force, such as four times a static force, for example. This hammer action allows for a smaller and/or lighter torsion spring 665, which allows for a lower actuation force to press the actuator 38. For example, if the momentum hammer force is four times a static force, then the user can press on the actuator 38 with four times less force. The snap action also generates a velocity of the sleeve 260 as it snaps back in the proximal direction. For example, it may be desirable that the sleeve 260 moves backward fast enough to generate a vacuum effect in order to pull tissue back with it. For example, the snap action may generate a sleeve tip velocity of 0.3 to 0.5 in/sec, such as 0.4 in/sec.

The damper spring 645 may serve multiple functions as well. For example, when the preload spring 635 force is released, the damper spring 645 dampens the force of the slidable housing 615 and the follower 631 as they snap in the proximal direction. In reverse, when the torsion spring 665 causes the internal mechanism 601 to reset, the damper spring 645 biases the follower 631 in the distal direction.

While the mechanism has been described with respect to implementations in which the internal mechanism 301, 401, 501, 601 is utilized to retract sleeve 260 (e.g., to pull a trabecular meshwork via a snapping motion like that described above with respect to the example of FIGS. 3A-3B), it will be appreciated that the mechanism may be suitably used for other modes of operation. For example, the snapping motion created by the mechanism can be utilized to snap the cannula 14 and/or sleeve 260 proximally and/or distally to create a vibration (e.g., upon impact of the follower 331, 431, 531, 631 against a stop) that facilitates penetration of the trabecular meshwork without a need for a suction effect. Thus, the follower 331, 431, 531, 631 can be fixedly coupled to the cannula 14 or any other suitable component for which motion is desired. It will also be appreciated that if the mechanism is employed for distal motion of the sleeve 260, cannula 14, or any other component, the various parts and operation of the mechanism can be reversed.

Figure 13:
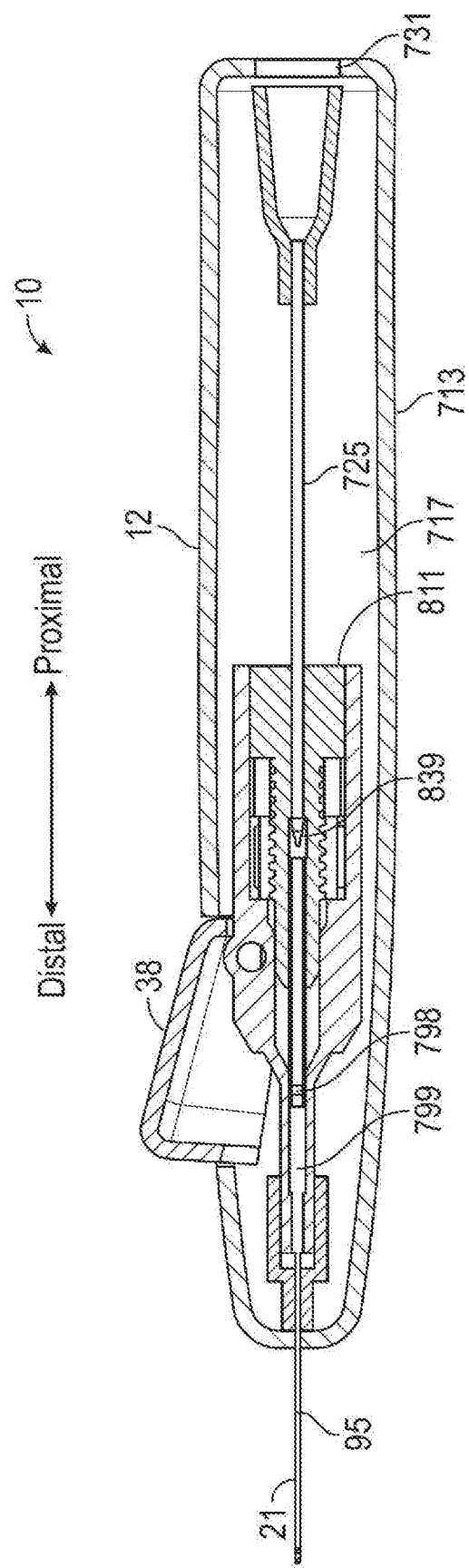
FIG. 13 is a longitudinal section view showing an example of an ophthalmic device.

FIG. 13 is a longitudinal section view showing an example of ophthalmic device 10. FIG. 13 shows an example of a structure for handle 12 and a fluid delivery mechanism that can be included in the handle 12 to facilitate delivery of a substance through the ocular component 21.

As shown in FIG. 13, the handle 12 can include a housing 713 that encloses and defines an internal volume 717. A lumen 725 (sometimes referred to herein as "handle lumen") can be disposed in the handle 12 and be fluidly coupled to the lumen 95 (sometimes referred to herein as "cannula lumen") protruding from the distal end of the handle 12. The handle lumen 725 can, for example, extend through the internal volume 717 and be configured to deliver fluid to the cannula lumen 95 from a fluid source, such as a fluid reservoir disposed within the internal volume or coupled to the handle externally.

As shown for example in FIG. 13, the handle 12 can include an inlet port 731 configured to couple to the fluid source and to receive an inlet fluid. The inlet port 731 can, for example, include a luer lock connector or any other suitable connector configured to connect to a viscoelastic syringe or any other suitable fluid reservoir. The inlet port 731 is shown in FIG. 13 disposed on a proximal end of the handle 12 so as to provide an inlet channel extending through an opening in a proximal end of the handle housing 713. Additionally or alternatively, the inlet port 731 can be disposed on another location on the handle 12, such as on a lateral sidewall of the handle 12. In the example shown in FIG. 13, the handle 12 holds a reservoir 799 that can be filled with an initial volume of fluid or other substance via the inlet port 731.

The handle 12 shown in FIG. 13 further includes a pump 811 which can be configured to move fluid through the handle lumen 725 and/or through the cannula lumen 95. For example as shown in FIG. 13, the pump 811 can include or be coupled to a piston 798 disposed within the internal volume 717 of the handle 12 and configured to translate in an axial direction proximally and/or distally. The piston pump can be configured to move in the distal direction from a proximal pump position to a distal pump position to draw fluid from the inlet port 731 and/or to urge or push fluid out through the distal end of the cannula lumen 95 and out through the orifice(s) 32. Thus, the pump 811 can be configured for positive and/or negative displacement of fluid. The piston 798 can also, for example, be reciprocal in the housing and configured to move in a proximal direction, from the distal pump position to the proximal pump position, so as to reset for delivering a subsequent dosage of fluid. Alternatively, the piston 798 can be configured to move incrementally in a distal direction in which each increment of distal motion corresponds to a dosage of fluid or other substance.

The pump 811 can include or be coupled to a valve 839 which can be disposed in the fluidic pathway of the handle lumen 725 and be fixedly coupled to the pump 811 so as to move together with the pump 811. The valve 839 can, for example, be implemented as or otherwise include a one-way valve (or "check valve") that permits fluid motion there through in a distal direction and restricts fluid motion there through in a proximal direction so as to create suction from the inlet port 731 and to force fluid out of the orifice(s) upon distal motion of the valve 839 together with the handle 12. Additionally or alternatively, it will be appreciated that various other types of pumps and/or fluid transfer mechanisms can be configured to move the fluid through the ophthalmic device 10.

The pump 811 can further be coupled to actuator 38 so as to permit actuation of the pump for delivery of a dosage or amount of fluid upon actuation of the actuator 38. The pump 811 can, for example, be coupled to the same actuator that moves the sleeve 260 or other part of the ocular component 21, or the pump 811 can be coupled to a separate actuator from that used to move the ocular component 21. In the example shown in FIG. 13, the actuator 38 includes a push button coupled to the pump 811 and configured trigger delivery of a discrete dosage of fluid upon user depression of the push button.

Figure 14A:
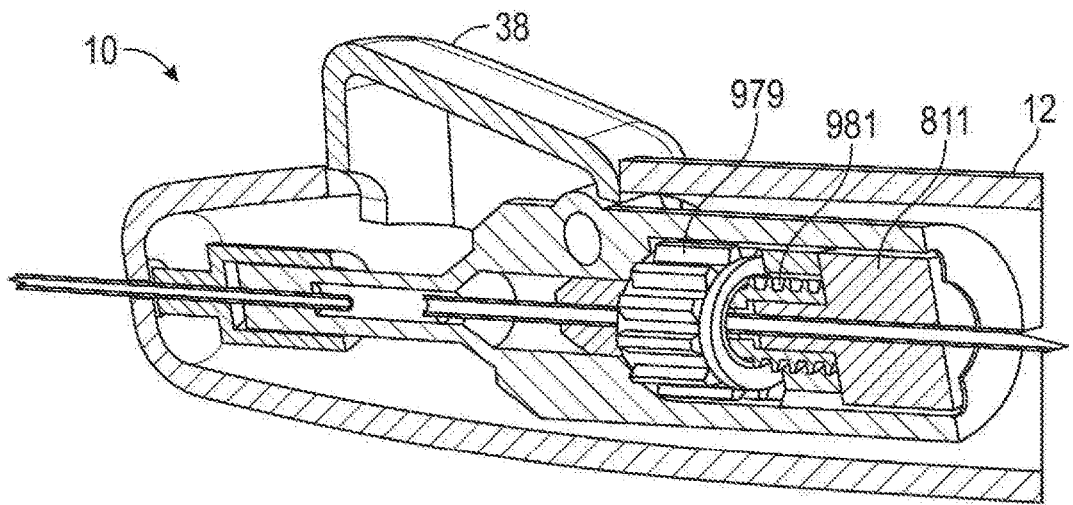
FIGS. 14A-14C are cutaway views showing an example of a mechanism configured to inject a fluid.
Figure 14B:
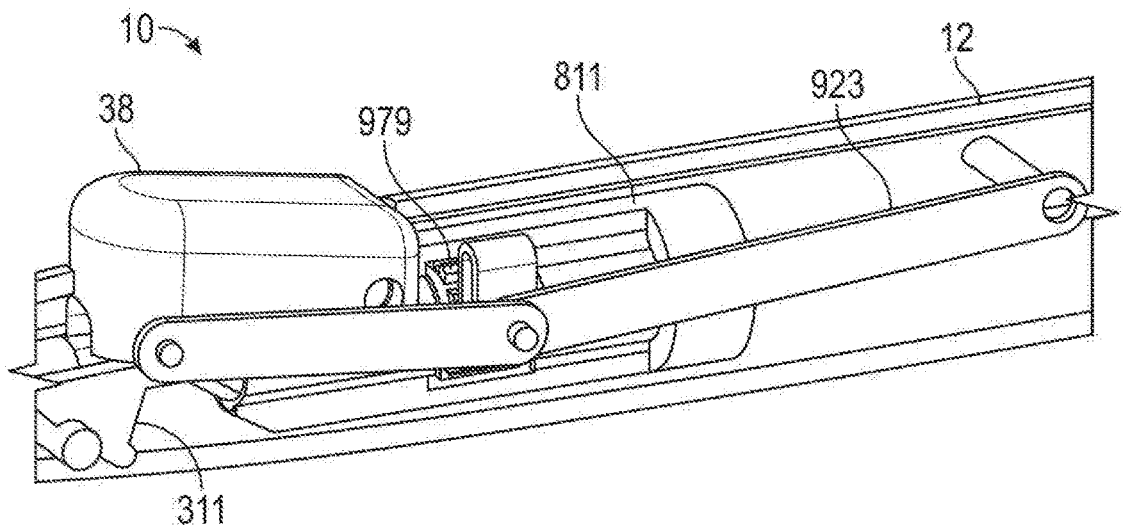
Figure 14C:
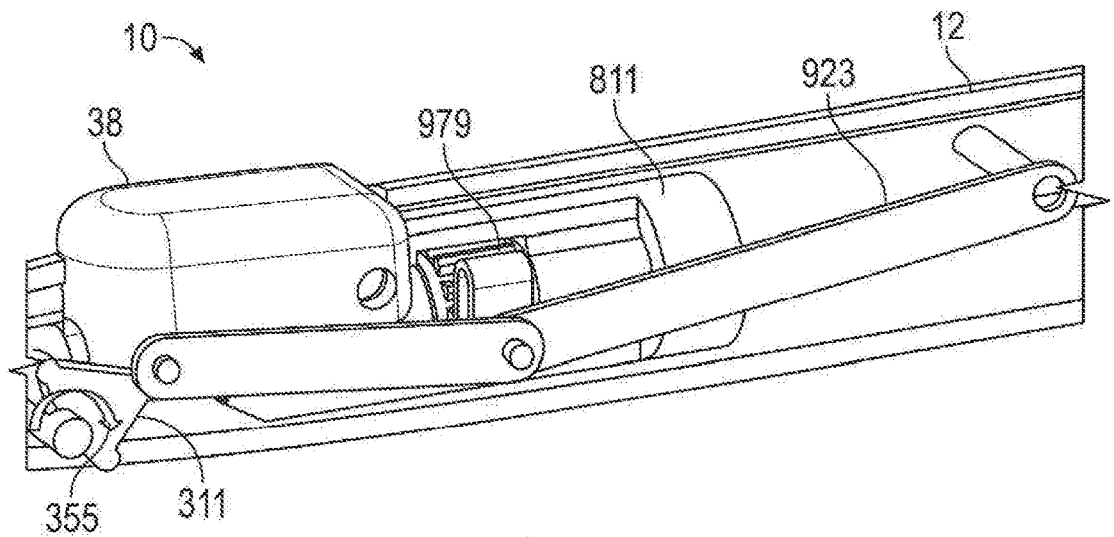

FIGS. 14A-14C are cutaway views of the handle 12 in which the actuator 38 is configured to actuate motion of the distal ocular component as well as the pump 811 in concert with each other. FIG. 14A is a cutaway view showing the internal mechanism with a linkage and cam removed for clarity. FIGS. 14B and 14C are cutaway views showing the internal mechanism with linkage 923 and cam 311 illustrated in an initial position before button press, and in an actuated position after button press, respectively.

The mechanism shown in FIGS. 14A-14C can be used so that each button press of the actuator 38 is a trigger that causes both retraction of the sleeve 260 (e.g., to pull trabecular meshwork 86 over the cannula 14 as shown in FIGS. 3A-3B) and delivery of a dosage of fluid through the cannula 14 while the sleeve 260 is retracted (e.g., while the trabecular meshwork 86 is pulled over the cannula 14 and the orifice(s) 32 are positioned within the Schlemm's canal 80 as shown in FIGS. 3A-3B). As shown for example in FIG. 14A, the mechanism can include a nut 979 coupled to a threaded portion 981 which is included in or fixedly coupled to the pump 811. The nut 979 can be mated with the threaded portion 981 so that rotation of the nut 979 drives axial motion of the pump 811 (e.g., translation in a distal direction) so as to cause the pump 811 to move fluid through the handle 12.

As shown in FIGS. 14B and 14C, the actuator 38 can be implemented as a push button coupled to the nut 979 via a linkage 723. As shown in FIGS. 14B and 14C, the same push button that drives the nut 979 can also be coupled to cam 311 of internal mechanism 301, arm 511, or rotatable housing 411, 611 directly or via the linkage 923. Upon a user force depressing the button from the un-pressed position shown in FIG. 14B to the pressed position shown in FIG. 14C, the push button can drive rotation of cam 311 in the first rotational direction 355 (e.g., to retract sleeve 260) and drive rotation of the nut 979 via the linkage 923, so as to move the piston 798 incrementally forward distally to move fluid through the handle 12 via positive displacement. Concurrently, the rotation of the cam 311 causes retraction of the sleeve 260 so the substance is delivered by the pump 811 while the sleeve 260 is in a retracted proximal position. Similarly, for internal mechanisms 401, 501 and 601, the same push button that drives the nut 979 can also be coupled to rotatable housing 411 of internal mechanism 401, arm 511 of internal mechanism 601, or rotatable housing 611 of internal mechanism 601, directly or via the linkage 923. Upon a user force depressing the button from the un-pressed position to the pressed position, the push button can drive rotation of the rotatable housing 411, the arm 511, or the rotatable housing 611, in the first rotational direction 455, 555, 655 (e.g., to retract sleeve 260) and drive rotation of the nut 979 via the linkage 923, so as to move the piston 798 incrementally forward distally to move fluid through the handle 12 via positive displacement.

Figure 15A:
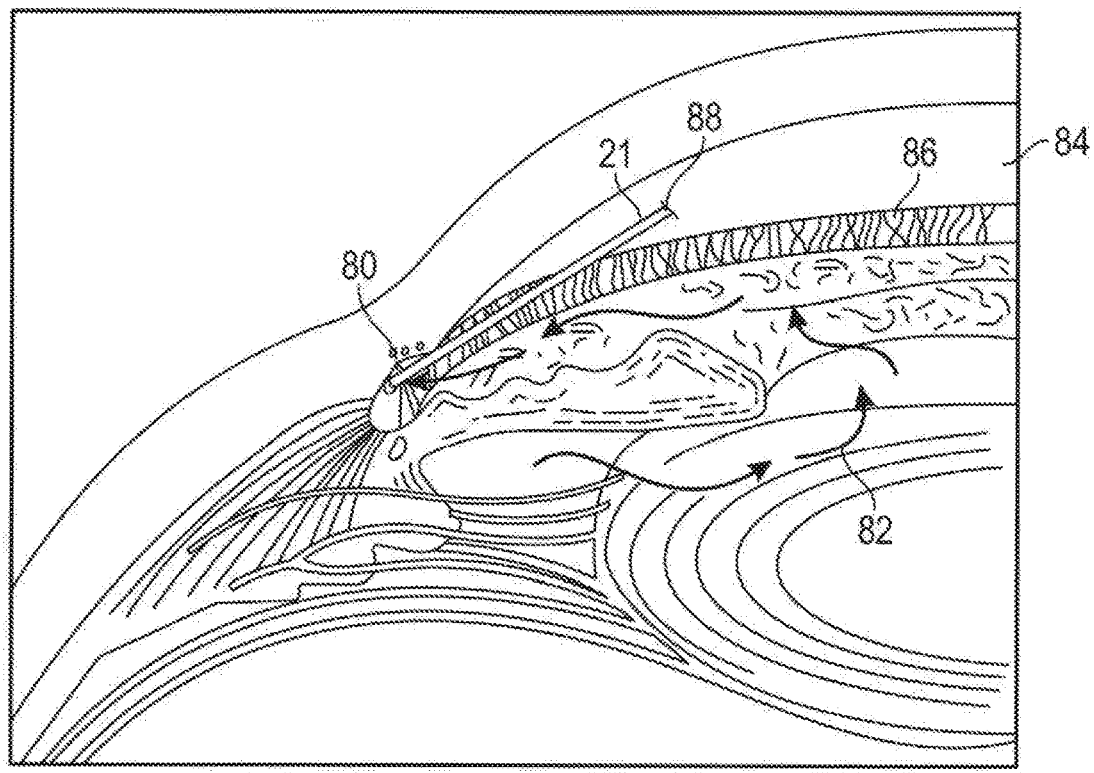
FIGS. 15A-15B are cutaway views showing an example of an ophthalmic procedure that can be performed with an ophthalmic device.
Figure 15B:
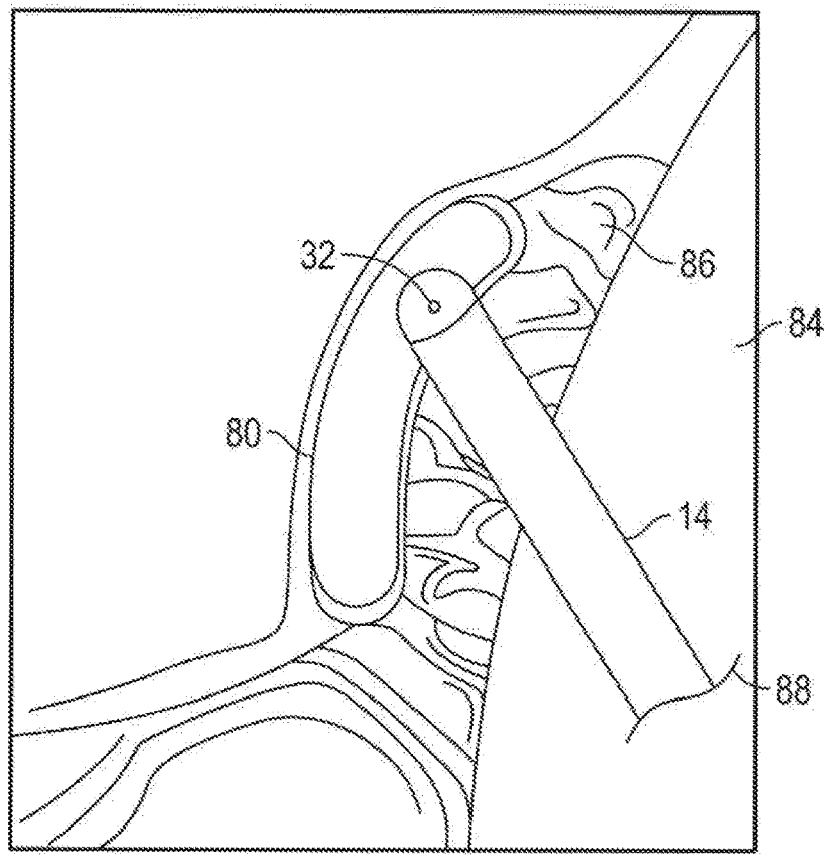

FIGS. 15A and 15B illustrate an exemplary method of performing an ophthalmic procedure using the ophthalmic device 10. The method can be used to deliver a substance (e.g., a fluid or gas) into, e.g., Schlemm's canal 80 or any other suitable portion of a patient's eye.

As noted above, in a healthy eye, a stream of aqueous humor 82 drains out of the anterior chamber 84 of the eye, through the trabecular meshwork 86 and then into Schlemm's canal 80 and distal collector channels. The aqueous humor 82 then exits through Schlemm's canal 80 into the collector channels and distal venous system. When this flow path of aqueous humor 82 is interrupted (e.g., due to diseased or damaged tissue in the trabecular meshwork 86 and/or Schlemm's canal 80), the IOP of an eye may rise, potentially resulting in a variety of medical concerns (e.g., glaucoma, loss of vision, optic nerve damage, etc.).

In order to improve the flow path of aqueous humor 82, a medical professional may insert ocular component 21 through an incision 88 made in the anterior chamber 84 and advance the distal end of sleeve 260 of the ocular component 21 to the trabecular meshwork 86 so that it abuts against or contacts the trabecular meshwork 86. The sleeve 260 (not visible in FIG. 15B) can then be retracted so that distal end of the cannula 14 including orifice(s) 32 enter the Schlemm's canal 80, as shown in FIG. 15B and as further described above using any of the mechanisms or components described herein.

With reference to FIG. 15B, once distal end of cannula 14 is inserted into Schlemm's canal 80 such that each of the one or more orifices 32 is fully housed within Schlemm's canal 80, the medical professional may inject a pre-defined dose or amount of fluid or other substance via actuation as discussed above. After injection of a pre-defined dose or amount of fluid or other substance through orifices 32, this process may be repeated any appropriate number of times, with the cannula 14 held in the same position and/or with the cannula 14 moved to one or more different positions to inject fluid in different locations and/or from different angles. Optionally, after the injection of one or more pre-defined doses of fluid or other substance at a certain location within Schlemm's canal 80, distal end of the cannula 14 may be retracted and repositioned within the eye. In some arrangements, such repositioning may occur via withdrawal of cannula 14 from incision 88 (e.g., a first incision), and reinsertion through an additional incision, spaced from the first incision. Additionally or alternatively, such repositioning may include retraction of distal end 30 from Schlemm's canal 80 and/or trabecular meshwork 86 and then relocation into a new portion of Schlemm's canal 80 without removal of cannula 14 from the first incision 88. In some implementations, fluid may be delivered into the Schlemm's canal 80 and trabecular meshwork 86 simultaneously, causing the Schlemm's canal 80 to open and deliver the fluid into the various layers of the trabecular meshwork 86.

It is to be understood that while the foregoing description describes devices and methods for injection of a fluid or other substance through orifices 32, the ophthalmic device 10 described herein may be arranged for precision-controlled aspiration of fluid or other substances away from the eye. For example, ophthalmic device 10 may be actuated in a reverse manner from that described above to achieve a removal of fluid or other substances from the eye.

One or more embodiments of the subject technology may include an ophthalmic device including a cannula having a cannula distal end, a lumen, and one or more orifices coupled to the lumen, the cannula configured to deliver a fluid; a sleeve disposed around the cannula and having a sleeve distal end; a handle coupled to the sleeve and the cannula, the handle having an actuator; and an internal mechanism coupled to the actuator and configured to retract the sleeve relative to the cannula. The internal mechanism may include a follower fixedly coupled to the sleeve and moveable between distal and proximal positions; and a release member movable between an activated position and a release position, the release member coupled to the actuator and configured to release a force that urges the follower from the distal position to the proximal position when the release member moves from the activated position to the release position.

One or more embodiments of the subject technology may include wherein the actuator includes a push button positioned on a lateral side of the handle and moveable from an un-pressed position to a pressed position upon application of a user force; and upon movement of the push button from the un-pressed position to the pressed position, the push button is configured to urge rotation of the release member in a first rotational direction.

One or more embodiments of the subject technology may include a reset spring coupled to the actuator, the reset spring configured to urge the push button from the pressed position back to the un-pressed position to urge rotation of the release member in a second rotational direction opposite the first rotational direction.

One or more embodiments of the subject technology may include wherein the cannula comprises a proximal shaft segment and a tip segment attached to proximal shaft segment; and the one or more orifices are disposed on the tip segment.

One or more embodiments of the subject technology may include a spring coupled to the follower and configured to apply a spring force to urge the follower in the proximal direction when the follower is in the distal position; a catch movable between a first position and a second position, the catch configured to hold the follower in the distal position when the catch is in the first position and to release the follower when the catch is in the second position; and the release member comprising a cam coupled to the catch, the cam configured to rotate in a first rotational direction against the catch to urge the catch from the first position to the second position.

One or more embodiments of the subject technology may include wherein the cam is further coupled to the follower; the catch is biased towards the second position; and upon release of a user force, the catch is configured to urge the cam against the follower in a second rotational direction opposite to the first rotational direction to urge the follower to from the proximal position to the distal position.

One or more embodiments of the subject technology may include a slidable housing having one or more first magnets and one or more second magnets; and the release member comprising a rotatable housing having one or more third magnets, wherein the slidable housing is configured to hold the follower in the distal position when the one or more third magnets are aligned with the one or more first magnets, and to urge the follower to the proximal position when the one or more third magnets are aligned with the one or more second magnets.

One or more embodiments of the subject technology may include wherein two first magnets are disposed 180 degrees apart in the slidable housing on a first plane that bisects a central axis of the slidable housing; two second magnets are disposed 180 degrees apart in the slidable housing on a second plane that bisects a central axis of the slidable housing; and two third magnets are disposed 180 degrees apart in the rotatable housing on a third plane that bisects a central axis of the rotatable housing.

One or more embodiments of the subject technology may include wherein the rotatable housing is configured to align the one or more third magnets with the one or more first magnets when the release member is in the activated position; and the rotatable housing is configured to align the one or more third magnets with the one or more second magnets when the release member is in the release position.

One or more embodiments of the subject technology may include a spring coupled to the follower and configured to apply a spring force to urge the follower in the proximal direction when the follower is in the distal position; a dowel pin movable between a first position and a second position, the dowel pin configured to hold the follower in the distal position when the dowel pin is in the first position and to release the follower when the dowel pin is in the second position; and the release member comprising an arm coupled to the dowel pin, the arm configured to rotate the dowel pin to urge the dowel pin from the first position to the second position.

One or more embodiments of the subject technology may include wherein the dowel pin comprises two rounded portions and two flat portions, wherein one of the rounded portions is configured to abut a proximal surface of the follower in the first position and one of the flat portions is configured to abut the proximal surface of the follower in the second position.

One or more embodiments of the subject technology may include wherein the dowel pin comprises an opening configured to receive the cannula, wherein the opening is configured to prevent the dowel pin from contacting the cannula during rotation of the dowel pin.

One or more embodiments of the subject technology may include the internal mechanism further having a slidable housing having a proximal surface comprising a first elevated portion and a first recessed portion; and the release member comprising a rotatable housing having a distal surface comprising a second elevated portion and a second recessed portion, wherein the slidable housing is configured to allow the follower to be disposed in the distal position when the first elevated portion is engaged with the second elevated portion, and to urge the follower to the proximal position when the first and second elevated portions are engaged with the first and second recessed portions, respectively.

One or more embodiments of the subject technology may include a first ramp portion disposed between the first elevated portion and the first recessed portion, wherein the second elevated portion is configured to slide along the first ramp from the first elevated portion to the first recessed portion when the rotatable housing is moved from the activated position to the release position.

One or more embodiments of the subject technology may include a second ramp portion disposed between the second elevated portion and the second recessed portion, wherein the first elevated portion is configured to slide along the second ramp from the second elevated portion to the second recessed portion when the rotatable housing is moved from the activated position to the release position.

One or more embodiments of the subject technology may include the internal mechanism further having a gap disposed between a distal facing surface of the follower and a proximal facing surface of the slidable housing when the follower is disposed in the distal position; and a spring coupled to the slidable housing and configured to apply a spring force to urge the slidable housing in the proximal direction when the follower is in the distal position, wherein the spring force is configured to cause the distal facing surface of the follower to accelerate through the gap and contact the proximal facing surface of the slidable housing with an impact force.

One or more embodiments of the subject technology may include wherein the spring force is configured to cause the sleeve to move backward at a velocity of 0.3-0.5 in/sec.

One or more embodiments of the subject technology may include a damper spring disposed proximally to the follower, the damper spring configured to dampen an impact force from the follower when the follower is moved to the proximal position and to bias the follower towards the distal position when the follower is in the proximal position.

One or more embodiments of the subject technology may include wherein the rotatable housing is configured to rotate 45 degrees in a first rotational direction about a central longitudinal axis of the cannula when the rotatable housing moves from the activated position to the release position.

One or more embodiments of the subject technology may include an internal mechanism for an ophthalmic device, the internal mechanism including: a slidable follower configured to be fixedly coupled to a sleeve disposed around a cannula, the slidable follower moveable between distal and proximal positions along a central longitudinal axis; a slidable housing having a proximal surface comprising a first elevated portion and a first recessed portion; a rotatable housing having a distal surface comprising a second elevated portion and a second recessed portion, the rotatable housing configured to be coupled to an actuator and movable between an activated position and a release position, wherein the first elevated portion is engaged with the second elevated portion in the activated position and the second elevated portion is engaged with the first recessed portion in the release position; a gap disposed between a distal facing surface of the follower and a proximal facing surface of the slidable housing when the follower is disposed in the distal position; and a spring coupled to the slidable housing and configured to apply a spring force to urge the slidable housing in the proximal direction when the follower is in the distal position, wherein the spring force is configured to cause the distal facing surface of the follower to accelerate through the gap and contact the proximal facing surface of the slidable housing with an impact force.

One or more embodiments of the subject technology may include an ophthalmic device comprising: a cannula having a cannula distal end, a lumen, and one or more orifices coupled to the lumen, the cannula being configured to inject a substance into a Schlemm's canal of an eye of a patient; a sleeve disposed around the cannula and having a sleeve distal end, the sleeve distal end being configured to contact a trabecular meshwork of the eye; and a handle coupled to the sleeve and the cannula, the handle having an actuator configured to retract the sleeve relative to the cannula to pull the trabecular meshwork over the cannula via a suction force.

One or more embodiments of the subject technology may include wherein an outer surface of the sleeve comprises one or more grooves configured to increase a surface area of the outer surface.

One or more embodiments of the subject technology may include wherein an outer surface of the sleeve comprises a plurality of circumferential grooves.

One or more embodiments of the subject technology may include wherein the sleeve distal end has an oblong cross section.

One or more embodiments of the subject technology may include wherein: the oblong cross section has a pair of opposing long sides and a pair of opposing short sides; the sleeve has a first pair of opposing outer surfaces converging towards the pair of opposing long sides; and the sleeve has a second pair of opposing outer surfaces diverging towards the pair of opposing short sides.

One or more embodiments of the subject technology may include wherein the one or more orifices include a pair of opposing orifices facing the pair of opposing short sides.

One or more embodiments of the subject technology may include wherein: the oblong cross section has a long outer diameter and a short outer diameter; the sleeve has a proximal portion with a proximal outer diameter; the long outer diameter is greater than the proximal outer diameter; and the short outer diameter is shorter than the proximal outer diameter.

One or more embodiments of the subject technology may include wherein: the cannula comprises a proximal shaft segment and a tip segment attached to proximal shaft segment; and the one or more orifices are disposed on the tip segment.

One or more embodiments of the subject technology may include wherein: the lumen of the cannula has a first portion disposed in the proximal shaft segment and a second portion disposed in the tip segment; and the first portion has a greater diameter than the second portion.

One or more embodiments of the subject technology may include a follower fixedly coupled to the sleeve and moveable between a distal position and a proximal position; a spring coupled to the follower and configured to apply a spring force to urge the follower in a proximal direction when the follower is in the distal position; a catch movable between a first position and a second position, the catch being configured to hold the follower in the distal position when the catch is in the first position and release the follower when the catch is in the second position; and a cam coupled to the catch, cam being configured to rotate against the catch to urge the catch from the first position to the second position.

One or more embodiments of the subject technology may include wherein: the actuator includes a push button positioned on a lateral side of the handle and moveable from an un-pressed position to a pressed position upon application of a user force; and upon movement of the push button from the un-pressed position to the pressed position, the push button is configured to urge rotation of the cam against the catch in a first rotational direction.

One or more embodiments of the subject technology may include wherein: the cam is further coupled to the follower; the catch is biased towards the second position; and upon release of the user force, the catch is configured to urge the cam against the follower in a second rotational direction opposite to the first rotational direction to urge the follower to from the proximal position to the distal position.

One or more embodiments of the subject technology may include wherein upon movement of the push button from the un-pressed position to the pressed position, the push button is further configured to move a pump to deliver a substance through the one or more orifices.

One or more embodiments of the subject technology may include a nut configured to drive the pump in a distal direction, wherein the push button is coupled to the nut via a linkage.

One or more embodiments of the subject technology may include wherein: the handle comprises a handle distal end and a handle proximal end; the cannula and the sleeve protrude from the handle distal end; and the handle comprises an inlet port fluidly coupled to the lumen.

One or more embodiments of the subject technology may include wherein: the inlet port is disposed on the handle proximal end; the handle comprises a pump coupled to the actuator; and the actuator is configured to actuate the pump to urge the substance through the one or more orifices.

One or more embodiments of the subject technology may include a method of performing an ophthalmic procedure, the method comprising: inserting a cannula and a sleeve into an anterior chamber of an eye through an incision; advancing a distal end of the sleeve to a trabecular meshwork of the eye; retracting the sleeve relative to the cannula; and pulling the trabecular meshwork over the cannula via a suction force applied with the retracting of the sleeve.

One or more embodiments of the subject technology may include injecting a substance into a Schlemm's canal of the eye through the cannula when the trabecular meshwork is pulled over the cannula.

One or more embodiments of the subject technology may include advancing the distal end of the sleeve against the trabecular meshwork and a scleral spur of the eye, wherein the distal end is sized small enough to enter an iridocorneal angle of the eye and large enough to avoid collapsing the trabecular meshwork into a Schlemm's canal of the eye.

One or more embodiments of the subject technology may include advancing the distal end of the sleeve against the trabecular meshwork; and collapsing the trabecular meshwork into a Schlemm's canal of the eye with the distal end of the sleeve, wherein the distal end is sized small enough to enter an iridocorneal angle of the eye and small enough to collapse the trabecular meshwork into the Schlemm's canal.

One or more embodiments of the subject technology may include an ophthalmic device comprising: a cannula having a cannula distal end, a lumen, and one or more orifices coupled to the lumen, the cannula being configured to inject a substance into an eye of a patient; a handle coupled to the cannula and having a handle distal end; and a lip protruding radially from an outer surface of the cannula and positionable between the cannula distal end and the handle distal end.

One or more embodiments of the subject technology may include wherein the lip is fixedly disposed between the cannula distal end and the handle distal end at an axial location proximal to at least one of the orifices.

One or more embodiments of the subject technology may include wherein: the lip is part of a retractable sleeve configured to move between a distal position and a proximal position; the lip is disposed at an axial location distal to at least one of the orifices when in the distal position; and the lip is disposed at an axial location proximal to the at least one of the orifices when in the proximal position.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f), unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirements of the applicable patent law, nor should they be interpreted in such a way.

What is claimed is:

1. An ophthalmic device comprising:
    a cannula having a cannula distal end, a lumen, and one or more orifices coupled to the lumen, the cannula configured to deliver a fluid;
    a sleeve disposed around the cannula and having a sleeve distal end;
    a handle coupled to the sleeve and the cannula, the handle having an actuator; and
    an internal mechanism coupled to the actuator and configured to retract the sleeve relative to the cannula, the internal mechanism comprising:
        a follower fixedly coupled to the sleeve and moveable between distal and proximal positions;
        a spring coupled to the follower and configured to apply a spring force to urge the follower in a proximal direction when the follower is in the distal position; and
        a release member movable between an activated position and a release position, the release member coupled to the actuator and configured to release a force that urges the follower from the distal position to the proximal position when the release member moves from the activated position to the release position, the release member comprising:
            a catch movable between a first position and a second position, the catch being configured to hold the follower in the distal position when the catch is in the first position and to release the follower when the catch is in the second position; and
            a cam coupled to the catch, the cam being configured to rotate against the catch to urge the catch from the first position to the second position.

2. The ophthalmic device of claim 1, wherein:
    the actuator includes a push button positioned on a lateral side of the handle and moveable from an un-pressed position to a pressed position upon application of a user force; and
    upon movement of the push button from the un-pressed position to the pressed position, the push button is configured to urge rotation of the release member in a first rotational direction.

3. The ophthalmic device of claim 2, further comprising:
    a reset spring coupled to the actuator, the reset spring configured to urge the push button from the pressed position back to the un-pressed position to urge rotation of the release member in a second rotational direction opposite the first rotational direction.

4. The ophthalmic device of claim 1, wherein:
    the cannula comprises a proximal shaft segment and a tip segment attached to proximal shaft segment; and
    the one or more orifices are disposed on the tip segment.

5. The ophthalmic device of claim 1, wherein the cannula is configured to inject the fluid into a Schlemm's canal of an eye of a patient, and wherein the sleeve distal end is configured to contact a trabecular meshwork of the eye.

6. The ophthalmic device of claim 1, wherein the cannula is configured to inject the fluid into a Schlemm's canal of an eye of a patient, and wherein the actuator is configured to retract the sleeve relative to the cannula to pull a trabecular meshwork of the eye over the cannula via a suction force.

7. The ophthalmic device of claim 1, wherein an outer surface of the sleeve comprises one or more grooves configured to increase a surface area of the outer surface.

8. The ophthalmic device of claim 1, wherein an outer surface of the sleeve comprises a plurality of circumferential grooves.

9. The ophthalmic device of claim 1, wherein the sleeve distal end has an oblong cross section.

10. The ophthalmic device of claim 9, wherein:
    the oblong cross section has a pair of opposing long sides and a pair of opposing short sides;
    the sleeve has a first pair of opposing outer surfaces converging towards the pair of opposing long sides; and
    the sleeve has a second pair of opposing outer surfaces diverging towards the pair of opposing short sides.

11. The ophthalmic device of claim 10, wherein the one or more orifices include a pair of opposing orifices facing the pair of opposing short sides.

12. The ophthalmic device of claim 9, wherein:
the oblong cross section has a long outer diameter and a short outer diameter;
the sleeve has a proximal portion with a proximal outer diameter;
the long outer diameter is greater than the proximal outer diameter; and
the short outer diameter is shorter than the proximal outer diameter.

13. The ophthalmic device of claim 9, wherein:
the cannula comprises a proximal shaft segment and a tip segment attached to the proximal shaft segment; and
the one or more orifices are disposed on the tip segment.

14. The ophthalmic device of claim 13, wherein:
the lumen of the cannula has a first portion disposed in the proximal shaft segment and a second portion disposed in the tip segment; and
the first portion has a greater diameter than the second portion.

15. The ophthalmic device of claim 1, wherein:
the actuator includes a push button positioned on a lateral side of the handle and moveable from an un-pressed position to a pressed position upon application of a user force; and
upon movement of the push button from the un-pressed position to the pressed position, the push button is configured to urge rotation of the cam against the catch in a first rotational direction.

16. The ophthalmic device of claim 15, wherein:
the cam is further coupled to the follower;
the catch is biased towards the second position; and
upon release of the user force, the catch is configured to urge the cam against the follower in a second rotational direction opposite to the first rotational direction to urge the follower from the proximal position to the distal position.

17. The ophthalmic device of claim 15, wherein:
upon movement of the push button from the un-pressed position to the pressed position, the push button is further configured to move a pump to deliver a substance through the one or more orifices.

18. The ophthalmic device of claim 17, further comprising:
a nut configured to drive the pump in a distal direction, wherein the push button is coupled to the nut via a linkage.

19. The ophthalmic device of claim 1, wherein:
the handle comprises a handle distal end and a handle proximal end;
the cannula and the sleeve protrude from the handle distal end; and
the handle comprises an inlet port fluidly coupled to the lumen.

20. The ophthalmic device of claim 19, wherein:
the inlet port is disposed on the handle proximal end;
the handle comprises a pump coupled to the actuator; and
the actuator is configured to actuate the pump to urge a substance through the one or more orifices.

* * * * *